United States Patent
Rein et al.

(10) Patent No.: US 6,316,190 B1
(45) Date of Patent: Nov. 13, 2001

(54) OLIGONUCLEOTIDES WHICH SPECIFICALLY BIND RETROVIRAL NUCLEOCAPSID PROTEINS

(75) Inventors: Alan Rein, Columbia; Jose Casas-Finet, Gaithersburg; Robert Fisher, Sharpsburg; Matthew Fivash, Frederick; Louis E. Henderson, Mount Airy, all of MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/180,903

(22) PCT Filed: May 19, 1997

(86) PCT No.: PCT/US97/08936

§ 371 Date: Jul. 12, 1999

§ 102(e) Date: Jul. 12, 1999

(87) PCT Pub. No.: WO97/44064

PCT Pub. Date: Nov. 27, 1997

Related U.S. Application Data

(60) Provisional application No. 60/017,128, filed on May 20, 1996.

(51) Int. Cl.[7] ............................. C12Q 1/68; C12P 21/06; C12N 15/00; C07H 21/02; A61K 39/42

(52) U.S. Cl. ..................... 435/6; 435/69.1; 435/69.7; 435/320.1; 536/23.1; 536/23.72; 424/160.1

(58) Field of Search ................ 435/6, 69.1, 69.7, 435/320.1; 536/23.1, 23.72; 424/160.1

(56) References Cited

FOREIGN PATENT DOCUMENTS

| WO 91/06318 | 5/1991 | (WO) | ........................... A61K/39/211 |
| WO 96/04294 | 2/1996 | (WO) | ........................... C07H/21/00 |
| WO 96/09406 | 3/1996 | (WO) | ........................... C12Q/1/18 |
| WO 93/22677 | 11/1993 | (WO) | ........................... G01N/33/531 |

OTHER PUBLICATIONS

Urbaneja et al., "HIV—1 Nucleocapsid (NC) protein p7 exhibits specific nucleic acid binding." 41st Annual Meeting of the Biophysical Society, New Orleans, Louisiana, USA, Mar. 2–6, 1997. *Biophysical Journal* 72 (2 Part 2), 1997.

(List continued on next page.)

*Primary Examiner*—Hankyel T. Park
(74) *Attorney, Agent, or Firm*—Townsend & Townsend & Crew LLP

(57) ABSTRACT

The invention provides oligonucleotides which bind to retroviral nucleocapsid proteins with high affinity, molecular decoys for retroviral nucleocapsid proteins which inhibit viral replication, targeted molecules comprising high affinity oligonucleotides, assays for selecting test compounds, and related kits.

37 Claims, 8 Drawing Sheets-

OTHER PUBLICATIONS

Urbaneja et al., "Interactions of HIV–1 Nucleocapsid Protein with Single–Stranded Nucleic Acids" 40th Annual Meeting of the Biophysical Society, Baltimore, Maryland, USA Feb. 17–21 1996) *Biological Abstracts*, vol. 98, Abstract No. 712756.

Casas–Finet et al., "Development of rapid screening assays for a new class of antiviral drugs attacking zinc fingers in retroviral nucleopsid proteins." 39th Annual Meeting of the Biophysical Society, San Francisco, CA, USA Feb. 12–16, 1995 *Biophysical Journal* 68 (2 Part 2) 1995.

Gorelick et al., "Roles of nucleocapsid cysteine arrays in retroviral assembly and replication: Possible mechanisms in RNA encapsidation" Advances in Molecular Biology and Targeted Treatment for AIDS, ed. Kumar, Plenum Press, New York (1991).

Fu et al., "Maturation of Dimeric Viral RNA of Moloney Murine Leukemia Virus" *Journal of Virology*, 67(9):5443–5449 (1993).

Fu et al., "Characterization of Human Immunodeficiency Virus Type 1 Dimeric RNA from Wild–Type and Protease–Defective Virions" *Journal of Virology*, 68(8):5013–5018 (1994).

Aldovini et al., "Mutations of RNA and Protein Sequences Involved in Human Immunodeficiency Virus Type 1 Packaging Result in Production of Noninfectious Virus" *Journal of Virology*, 64(5):1920–1926 (1990).

McBride, et al., "The Human Immunodeficiency Virus Type 1 Encapsidation Site is a Multipartite RNA Element Composed of Functional Hairpin Structures" *Journal of Virology*, 70(5):2963–2973 (1996).

Berkwoitz, et al., "Specific Binding of Human Immunodeficiency Virus Type 1 gag Polyprotein and Nucleocapsid Protein to Viral RNAs Detected by RNA Mobility Shift Assays" *Journal of Virology*, 61(12):7190–7200 (1993).

Berkowitz, et al., "Analysis of Binding Elements in the Human Immunodeficiency Virus Type 1 Genomic RNA and Nucleocapsid Protein" *Virology*, 202:233–246 (1994).

Fisher, et al., "Surface plasmon resonance based methods for measuring the kinetics and binding affinities of biomolecular interactions" *Current Opinion in Biotechnology*, 5:389–395 (1994).

Fisher, et al. "Real–Time BIAcore Measurements of *Escherichia coli* Single–Stranded DNA Binding (SSB) Protein to Polydeoxythymidylic Acid Reveal Single–State Kinetics with Steric Cooperativity" *Methods*, 6:121–133 (1994).

```
                          SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
         (A) LENGTH: 14 amino acids
         (B) TYPE: amino acid
         (C) STRANDEDNESS: <Unknown>
         (D) TOPOLOGY: linear (ii) MOLECULE TYPE: peptide (xi) SEQUENCE DESCRIPTION: SEQ ID NO: 1:

Cys Xaa Xaa Cys Xaa Xaa Xaa Xaa His Xaa Xaa Xaa Xaa Cys
1               5                   10

(2) INFORMATION FOR SEQ ID NO: 2:

(i) SEQUENCE CHARACTERISTICS:
         (A) LENGTH: 4 amino acids
         (B) TYPE: amino acid
         (C) STRANDEDNESS: <Unknown>
         (D) TOPOLOGY: linear (ii) MOLECULE TYPE: peptide (xi) SEQUENCE DESCRIPTION: SEQ ID NO: 2:

Cys Cys His Cys
1

(2) INFORMATION FOR SEQ ID NO: 3:

(i) SEQUENCE CHARACTERISTICS:
         (A) LENGTH: 4 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO: 3:

TGTG                                                          4
```

(2) INFORMATION FOR SEQ ID NO: 4:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

```
TGTGT                                                          5
```

(2) INFORMATION FOR SEQ ID NO: 5:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

```
GTGTG                                                          5
```

(2) INFORMATION FOR SEQ ID NO: 6:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

```
TGTGTGTG                                                       8
```

(2) INFORMATION FOR SEQ ID NO: 7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

```
TGTGTGTGTG                                                    10
```

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

```
TGTGTGTGTG TGTGTGTGTG                                         20
```

(2) INFORMATION FOR SEQ ID NO: 9:

(i) SEQUENCE CHARACTERISTICS:
    (A) LENGTH: 6 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 9:

TGTGTG                                                        6

(2) INFORMATION FOR SEQ ID NO: 10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

GACTTGTGGA                                                    10

(2) INFORMATION FOR SEQ ID NO: 11:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 11:

GACUUGUGG                                                     9

(2) INFORMATION FOR SEQ ID NO: 12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

TTTTTTTTTT                                                    10

(2) INFORMATION FOR SEQ ID NO: 13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

AAAATGTGAA                                                    10

(2) INFORMATION FOR SEQ ID NO: 14:

(i) SEQUENCE CHARACTERISTICS:
        (A) LENGTH: 10 base pairs
        (B) TYPE: nucleic acid
        (C) STRANDEDNESS: single

```
            (D) TOPOLOGY: linear (ii) MOLECULE TYPE: DNA (xi) SEQUENCE DESCRIPTION: SEQ ID NO: 14:

GACTAAAAGA                                                              10

(2) INFORMATION FOR SEQ ID NO: 15:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 15:

AAAATCTCTA                                                              10
```

OLIGONUCLEOTIDES WHICH SPECIFICALLY BIND RETROVIRAL NUCLEOCAPSID PROTEINS

CROSS REFERENCE TO RELATED APPLICATIONS

This application is a continuation-in-part of U.S. Provisional Patent Application U.S. Ser. No. 60/017,128 by Rein et al. filed May 20, 1996. The disclosure of U.S. Ser. No. 60/017,128 is incorporated herein by reference for all purposes.

FIELD OF THE INVENTION

The present invention relates to the fields of molecular biology, immunology, retrovirus biology, and biochemistry.

BACKGROUND OF THE INVENTION

A single retroviral protein species, the Gag polyprotein, is sufficient for assembly of retrovirus particles. Since this process includes the selective encapsidation of viral RNA, this protein is evidently capable of specific interactions with nucleic acids. The nature of these interactions is not well understood as yet. After the virion is released from the cell, the polyprotein is cleaved by the virus-coded protease; one of the cleavage products, termed the nucleocapsid (NC) protein, then binds to the genomic RNA, forming the ribonucleoprotein core of the mature particle.

The interaction between Gag and genomic RNA is known to involve the NC domain of the polyprotein, since mutants within NC are defective in RNA packaging and since the specificity of encapsulation tends to be determined by the NC domain in chimeric Gag molecules. However, NC is a basic protein and has frequently been described as binding to single-stranded DNA or RNA in a sequence-independent manner. Indeed, it has been hypothesized to be capable of binding to any single-stranded nucleic acid under appropriate conditions. This binding activity appears to be important at several stages of virus replication.

A search of all known retroviruses reveals a highly conserved structure in their NC proteins. All NC proteins of the Oncovirinae and Lentivirinae subfamilies of Retroviridae contain one or two copies of a conserved sequence motif termed the "cysteine array" or "Cys-His box." This motif can be represented as $Cys(X)_2Cys(X)_4His(X)_4Cys$ (SEQ ID NO:1) (Henderson et al., *J. Biol. Chem.*, 256:8400 (1981)). This motif is also known as the NC zinc finger or, alternatively, as the retroviral CCHC (SEQ ID NO:2) zinc finger because it chelates zinc through histidine imidazole and cysteine thiolates with a $K_d$ less than $10^{-13}$ (Berg, *Science*, 232:485 (1986); Bess, Jr., et al., *J. Virol.*, 66:840 (1992); Chance, et al., *Proc. Natl. Acad. Sci. U.S.A.*, 89:10041 (1992); South, et al., *Adv. Inorg. Biochem.*, 8:199 (1990); South, et al., *Biochem. Pharmacol.*, 40:123 (1990)). Examples of retroviruses which possess at least one CCHC (SEQ ID NO:2) type zinc finger per nucleocapsid protein include, but are not limited to, HIV-1, HIV-2, SIV, BIV, EIAV, Visna, CaEV, HTLV-1, BLV, MPMV, MMTV, RSV, MuLV, FeLV, BaEV, and SSV.

The function of the NC zinc finger is not yet fully understood. However, all mutations in the zinc-binding residues which been described to date have been lethal for the virus. Virions produced by these mutants are frequently defective with respect to genomic RNA content (Aldovini, et al., *J. Virol.*, 64:1920–1926 (1990); Dorfman, et al., *J. Virol.*, 67:6159–6169 (1993); Dupraz, et al., *J. Virol.*, 64:4978–4987 (1990); Gorelick, et al., *Proc. Natl. Acad. Sci. USA*, 85:8420–8424 (1988); Gorelick, et al., *J. Virol.*, 46:3207–3211 (1990); Méric, et al., *J. Virol.*, 63:1558–1568 (1989). As such, it is thought that the zinc fingers participate (as part of the Gag polypeptide precursor) in RNA packaging during virion assembly. Significantly, however, the mutant particles are far more defective with respect to infectivity than with respect to genomic RNA content (Gorelick, et al., *Proc. Natl. Acad. Sci. USA*, 85:8420–8424 (1988)). A new class of zinc-finger mutants of Moloney MuLV (Mo-MuLV) have recently been characterized (Gorelick, et al. (1996) *J. Virol.* 70:2593–2597), and indeed, it has been found that these mutants package normal levels of genomic RNA, but are nevertheless noninfectious. Such observations imply that the zinc fingers play other roles in the viral life cycle in addition to their function in RNA packaging. It has been suggested that NC has an important role in maturation of the released virus particle (Fu, et al., *J. Virol.*, 68:5013–5018 (1994); Fu and Rein, *J. Virol.*, 67:5443–5449 (1993)), and performs one or more functions in reverse transcription (Allain, et al., *EMBO J.*, 13:973–981 (1994); Lapadat-Tapolsky, et al., *Nucleic Acids Res.*, 21:831–839 (1993); Nagy, et al., *J. Virol.*, 68:757–765 (1994); Peliska, et al., *Biochemistry*, 33:13817–13823 (1994); Roberts, et al., *Biochem. Biophys. Res. Commun.*, 160:486–494 (1989); Rodriguez-Rodriguez, et al., *J. Biol. Chem.*, 270:15005–15011 (1995); You, et al., *J. Biol. Chem.*, 269:31491–31495 (1994); Wu et al. (1996) *J. Virol.* 7132–7142). To date, however, the significance of the zinc finger and, in turn, the NC protein is not fully understood, nor is the binding of NC to nucleic acids.

SUMMARY OF THE INVENTION

The present invention stems from the surprising discovery that retroviral nucleocapsid proteins, such as NC and the Gag precursor, bind to specific nucleic acid sequences with high affinity. In the results described herein, the binding of recombinant HIV-1 NC protein to short oligonucleotides is assessed. These studies were typically performed at moderate ionic strengths, at which the nonspecific electrostatic interaction between NC and nucleic acids is minimized. Under these conditions, the protein exhibits profound sequence preferences. This sequence-specific binding is dependent upon the zinc fingers of the NC protein and has a strong hydrophobic component.

In one aspect, specific nucleic acid sequences which bind NC are useful as molecular decoys for retroviral nucleocapsid proteins, for making fusion molecules which inactivate retroviral nucleocapsid proteins, in screening assays for detecting molecules which inactivate retroviral nucleocapsid protein nucleic acid binding, and for purification of retroviral nucleocapsid proteins.

Example oligonucleotides which specifically bind retroviral nucleocapsid protein include oligonucleotides comprising the sequences TGTG (SEQ ID NO:3), TGTGT (SEQ ID NO:4), GTGTG (SEQ ID NO:5), $(TG)_4$ (SEQ ID NO:6), $(TG)_5$ (SEQ ID NO:7), $(TG)_{10}$ (SEQ ID NO:8), TGTGTG (SEQ ID NO:9), GACTTGTGGA (SEQ ID NO:10), and GACUUGUGG (SEQ ID NO:11). Examples of retroviruses which possess nucleocapsid proteins include, but are not limited to, HIV-1, HIV-2, SIV, BIV, EIAV, Visna, CaEV, HTLV-1, BLV, MPMV, MMTV, RSV, MuLV, FeLV, BaEV, and SSV.

In one embodiment, the invention provides a targeted molecule comprising an oligonucleotide which binds to a retroviral nucleocapsid protein with high affinity, and a fusion partner. The targeted molecule binds to the retroviral nucleocapsid protein with high affinity. Example retroviral nucleocapsid proteins include the Gag and NC proteins from HIV-1, HIV-2, SIV, BIV, EIAV, Visna, CaEV, HTLV-1, BLV, MPMV, MMTV, RSV, MuLV, FeLV, BaEV, and SSV.

The fusion partner optionally reacts with the retroviral nucleocapsid protein, thereby reducing the ability of the nucleocapsid protein to package retroviral RNA. This is accomplished by disrupting the viral nucleic acid binding site through altering amino acid side chains in the nucleocapsid nucleic acid binding site, or by attaching the targeted molecule to the binding site and sterically inhibiting nucleic acid binding of the retroviral nucleocapsid protein.

Alternatively, the fusion partner is optionally a cytotoxic molecule which is sequestered to cells comprising retroviral nucleocapsid proteins (e.g., a retrovirally infected cell), thereby killing the cell and preventing retroviral replication in the cell.

In one embodiment, the fusion partner does not react with the nucleocapsid protein, but is simply a label, such as a biotin or dye molecule. In this embodiment, the targeted molecule is used to visualize nucleocapsid proteins by binding the targeted molecule comprising a label to the nucleocapsid protein. In other embodiments, the targeted molecule comprises an oligonucleotide specific for nucleocapsid proteins, a fusion partner, and a label. In this embodiment, the fusion partner is optionally reactive with the nucleocapsid protein, and the label is available for visualizing nucleocapsid-targeted molecule interactions.

The invention provides expression vector nucleic acids encoding the oligonucleotides of the invention. Typically, the expression vectors comprise a nucleic acid sequence to be expressed (i.e., which encodes an oligonucleotide of the invention) and sequences for controlling expression of the vector nucleic acid in a cell. For example, the vector is optionally expressed in a mammalian cell using a mammalian promoter to direct expression in the mammalian cell.

In one embodiment, the vector is a therapeutic nucleic acid which expresses oligonucleotides which bind a retroviral nucleocapsid in the cell. In this embodiment, the expressed oligonucleotide acts as a molecular decoy for retroviral nucleocapsid proteins. The vector optionally comprises protein or lipid components such as a viral particle to facilitate delivery of the nucleic acid into a cell. In a preferred embodiment, the vector comprises a retroviral particle.

The invention also comprises cells which include the nucleic acids or oligonucleotides of the invention. Preferred cells are those of primate or rodent origin, particularly those of human origin. In one class of embodiments, the vectors of the invention are used to produce stem cells or CD4+ cells which express the oligonucleotides of the invention.

Assays are provided by the invention. In the assays, target molecules are assessed for their ability to inhibit binding of retroviral nucleocapsid proteins to selected nucleic acids. In the assays, retroviral nucleocapsid proteins, oligonucleotides comprising a subsequence which binds to a retroviral nucleocapsid protein with high affinity, and a target molecule are mixed, and the inhibitory effect on nucleocapsid-oligonucleotide binding is measured. Example molecules include any which may potentially disrupt retroviral nucleocapsid-oligonucleotide interactions, including oligonucleotides, proteins, and organic compounds. In one particularly preferred embodiment, the assay format is plasmon resonance. In another particularly preferred embodiment, the assays are performed in parallel on a number of samples. I(its for performing the assays of the invention comprising compositions of the invention, containers, instructions in practicing the assay methods of the invention, and the like are also provided.

Methods of detecting and purifying a nucleocapsid protein are provided. In the methods, the specific binding of an oligonucleotide to the nucleocapsid protein is detected, or the specific oligonucleotide is used as a molecular tag to purify the protein. Typically, the oligonucleotide is labelled, permitting detection of the nucleocapsid protein by detecting the label. In a preferred embodiment, this detection method provides a means of detecting or purifying HIV from a patient, e.g., from a blood sample. Either intact virus, or a nucleocapsid protein (NC, Gag precursor, etc.) is detected or purified.

DEFINITIONS

Figure 1:
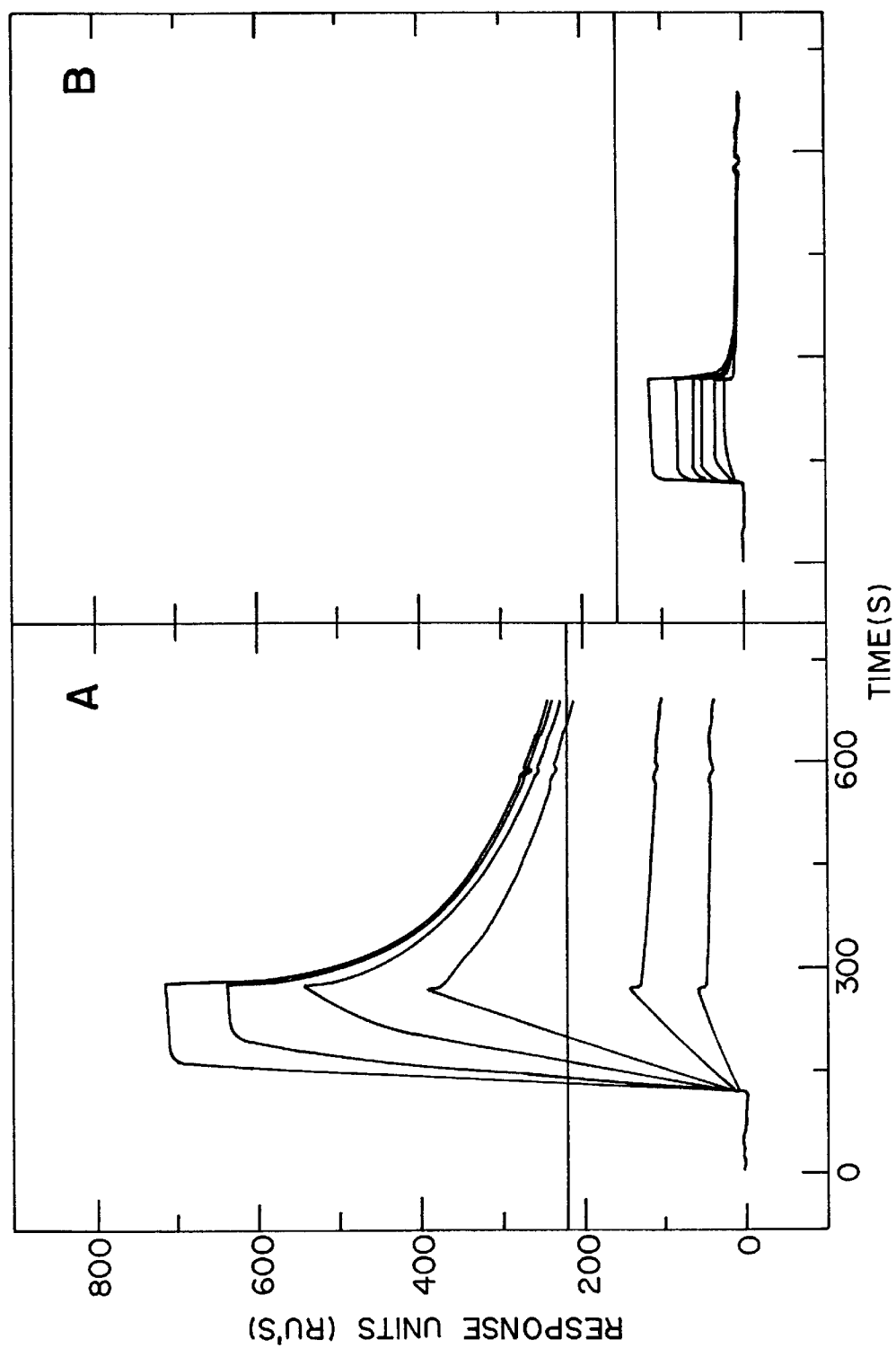
FIG. 1, Panels A and B show graphs of NC binding to ss 28 mer.

Unless defined otherwise, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York); Walker (ed) (1988) The *Cambridge Dictionary of Science and Technology*, The press syndicate of the University of Cambridge, N.Y.; and Hale and Marham (1991) The Harper Collins Dictionary of Biology Harper Perennial, N.Y. provide one of skill with a general dictionary of many of the terms used in this invention. Paul (1993) *Fundamental Immunology*, Third Edition Raven Press, New York, N.Y. and the references cited therein provide one of skill with a general overview of the ordinary meaning of many of the virally or immunologically related terms herein. Although any methods and materials similar or equivalent to those described herein can be used in the practice or testing of the present invention, preferred methods and materials are described. For purposes of the present invention, the following terms are defined below.

A "targeted molecule" is a molecule which has an element which binds to a retroviral nucleocapsid protein with high affinity. For example, a molecule which comprises an oligonucleotide that binds to an NC protein with high affinity is a targeted molecule.

A "target" molecule in an assay of the invention refers generically to any molecule to be tested in the assay, e.g., for inhibition of binding of an NC protein to an oligonucleotide which specifically binds to the NC protein.

A "high affinity" binding interaction of a molecule of the invention with a nucleocapsid protein indicates that the molecule binds the NC protein with an affinity at least about 100 times as high as a non-specific molecule. For example, a high affinity oligonucleotide binds to a NC protein with an affinity at least about 100 times as high as a non-specific CA rich sequence of similar length. Affinities are tested by standard techniques such as surface plasmon resonance. Often the affinity may be about 1,000 times as high and sometimes 10,000 times as high.

A "retroviral nucleocapsid protein" is a protein which includes a retroviral nucleocapsid sequence, or subsequence. Example proteins include the NC protein and the retroviral Gag precursor which is cleaved to produce the NC protein during the retroviral life cycle.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. An "oligonucleotide" is a nucleic acid. Although an oligonucleotide is optionally of any length, oligonucleotides are typically between about 3 and about 300 nucleotides in length. Often, oligonucleotides are between about 5 and about 100 nucleotides in length. Generally, oligonucleotides are between about 6 and about 40 nucleotides in length. A "recombinant nucleic acid" is a nucleic acid made by joining heterologous nucleic acid subsequences, e.g., by ligation, cloning, or synthetically synthesizing the nucleic acid. Heterologous nucleic acid subsequences are nucleic acid subsequences which are not found next to each other in naturally occurring nucleic acids.

A "fusion partner" is a molecule to be joined, covalently or non-covalently, to an oligonucleotide which binds a retroviral nucleocapsid protein with high affinity. After joining, the fusion partner portion of the resulting oligonucleotide-fusion partner is still referred to as a fusion partner, or optionally as a fusion partner domain.

A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

A "constitutive" promoter is a promoter which is active under most environmental and developmental conditions. An "inducible" promoter is a promoter which is under environmental or developmental regulation.

The terms "isolated" or "biologically pure" refer to material which is substantially or essentially free from components which normally accompany it as found in its native state.

A "nucleic acid which encodes an oligonucleotide" is a nucleic acid which comprises either the sense or anti-sense strand of a selected oligonucleotide. The term also includes any RNA or DNA version of the oligonucleotide (which may be RNA or DNA) or an RNA or DNA analogue thereof, or any transcription cassette which is competent to transcribe an RNA corresponding to the oligonucleotide.

A nucleocapsid "molecular decoy" is a molecule which competes with the natural binding sites for retroviral nucleocapsid proteins (i.e., retroviral genomic RNA). An "oligonucleotide molecular decoy" is an oligonucleotide which binds to retroviral nucleocapsid proteins (and preferably to Gag) with high affinity. Because the molecular decoy competes with the natural binding site for Gag proteins, the decoy inhibits the natural packaging functions of the protein, thereby inhibiting viral replication.

"Independently mixing" in the context of a parallel assay indicates that the components of two assays are mixed in separate systems. For example, two parallel assays are optionally performed in two separate wells on a microtiter dish.

A "label" is a composition detectable by spectroscopic, photochemical, biochemical, immunochemical, or chemical means. For example, useful labels include 32P, 35S, fluorescent dyes, chromophores, electron-dense reagents, enzymes (e.g., as commonly used in an ELISA), biotin, dioxigenin, or haptens and proteins for which antisera or monoclonal antibodies are available. In some preferred embodiments, labels are detectable spectroscopically, i.e., they are chromogenic. Suitable chromogens include molecules and compounds which absorb light in a distinctive range of wavelengths so that a color may be observed, or emit light when irradiated with radiation of a particular wavelength or wavelength range (e.g., a fluorescent label). Fluorescent moieties, which are incorporated into the labels of the invention are generally are known. Many fluorescent tags are commercially available from the SIGMA chemical company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc. (Sterling, Va.), GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.) as well as other commercial sources known to one of skill.

A "GT rich" oligonucleotide is an oligonucleotide which is composed entirely, or largely of G or T nucleotides. For example, such oligonucleotides are preferably at least about 80%, sometimes 90% and occasionally 95% or more GT. Similarly, a "GU rich" oligonucleotide is an oligonucleotide composed entirely, or largely, of G and U nucleotides. For example, such oligonucleotides are preferably at least about 80%, sometimes 90% and occasionally 95% or more GU.

DETAILED DESCRIPTION OF THE INVENTION AND PREFERRED EMBODIMENTS

Prior art analysis of NC-nucleic acid interactions suggested that NC proteins boud to single stranded nucleic acids non-specifically. Surprisingly, this invention reveals that specific single stranded nucleic acid sequences (both RNA and DNA) bind NC specifically. As demonstrated herein, certain sequences as short as tetramers can specifically bind NC proteins under specific conditions, although sequences which are, at least, pentamers are preferable. Pentamer and hexamer sequences, as well as longer sequences such as heptamers and octamers are also shown to specifically bind to NC proteins.

The discovery of specific oligonucleotides which specifically bind NC provides for the synthesis and use of many related compounds. For example, a specific oligonucleotide further comprising a fusion partner can target the NC protein, providing for specific detection of the NC protein, and for colocalization of the NC protein and the oligonucleotide fusion, both in vitro and in vivo. For example, by targeting cytotoxic fusion partners to NC proteins it is possible to selectively kill cells which comprise the fusion proteins. This is of use in vitro as a negative selectable marker (or as a positive selectable marker where the fusion partner provides a selective advantage). In vivo, the delivery of a specific delivery of a cytotoxic agent to cells comprising an NC protein is of benefit in the treatment of individuals infected with a virus comprising an NC protein, including HIV-1 and HIV-2. Similarly, a specific oligonucleotide acts as a molecular decoy for NC proteins, thereby inhibiting packaging of wild-type genomic RNA.

Accordingly, the present invention provides, inter alia, oligonucleotides which specifically bind to NC proteins, targeted molecules comprising such oligonucleotides and a fusion partner, methods of inhibiting cell growth of cells infected with viruses comprising NC proteins, assays for the discovery of specific oligonucleotides and targeted molecules, and related kits.

Making Nucleic Oligonucleotides, Nucleic Acids Encoding Oligonucleotides, and Retroviral Nucleocapsid Proteins Oligonucleotides of the invention are typically synthesized chemically according to the solid phase phosphoramidite triester method described by Beaucage and Caruthers (1981), *Tetrahedron Letts.*, 22(20):1859–1862, e.g., using an automated synthesizer, as described in Needham-VanDevanter et al. (1984) *Nucleic Acids Res.*, 12:6159–6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560. The oligonucleotides of the invention are also synthesized recombinantly. Long oligonucleotides (100 to 300 nucleotides or larger) are typically produced recombinantly.

Preferred oligonucleotides of the invention comprise a sequence selected from the group consisting of TGTG (SEQ ID NO:3), TGTGT (SEQ ID NO:4), GTGTG (SEQ ID NO:5), $(TG)_4$ (SEQ ID NO:6), $(TG)_5$ (SEQ ID NO:7), $(TG)_{10}$ (SEQ ID NO:8), TGTGTG (SEQ ID NO:9), GACT-TGTGGA (SEQ ID NO:10), and GACUUGUGG (SEQ ID NO:11). One of skill will appreciate that oligonucleotides containing multiple copies of the given sequences are also preferred. Typically, the oligonucleotides will be single stranded, but dimers of viral RNA also specifically bind NC proteins.

Preferred oligonucleotides optionally comprise additional sequences. Additional sequences are optionally chosen such that extensive hairpin formation in the preferred sequence portions the oligonucleotide does not occur. This is accomplished by excluding oligonucleotides which have regions of self complementarity.

Oligonucleotides are optionally selected in pairs which dimerize. Retroviral nucleocapsid proteins may specifically bind to dimer nucleic acids, particularly to dimers of RNA. Oligonucleotides dimerize when they include nucleic acids which base-pair in solution.

One of skill can construct a variety of clones containing nucleic acids which express the oligonucleotides of the invention. Typically, a nucleic acid encoding a selected oligonucleotide is cloned under the control of a promoter which directs transcription of the nucleic acid. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning-A Laboratory Manual* (2nd ed.) Vol. 1–3, Cold Spring Harbor Laboratory, Cold Spring Harbor Press, N.Y., (Sambrook); and *Current Protocols in Molecular Biology*, F.M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

The nucleic acid compositions of this invention, whether RNA, cDNA, genomic DNA, or a hybrid of the various combinations, are isolated from biological sources or synthesized in vitro. The nucleic acids of the invention are present in transformed or transfected whole cells, in transformed or transfected cell lysates, or in a partially purified or substantially pure form.

In vitro amplification techniques suitable for amplifying sequences for use in generating nucleic acid fragments for subsequent subcloning are also known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. Improved methods of amplifying large nucleic acids are summarized in Cheng et al. (1994) *Nature* 369: 684–685 and the references therein. One of skill will appreciate that essentially any RNA can be converted into a double stranded DNA suitable for restriction digestion, PCR expansion and sequencing using reverse transcriptase and a polymerase. Similarly, essentially any RNA can be produced by cloning a corresponding DNA nucleic acid downstream from the start site of transcription in a vector which has a promoter. Where desired, a splice site can be incorporated to separate a nucleic acid subsequence of interest from a larger expressed RNA. See, Ausubel, Sambrook and Berger, all supra.

The nucleic acids of the invention typically include transcription cassettes which are expressed by the cell to be transformed. The transcription cassettes preferably include constitutive or inducible promoters. Illustrative promoters include pol III promoters (e.g., those from the t-RNA genes, such as t-RNAval), HIV LTR promoters, the SV-40 promoter (*Science* (1983) 222:524–527), the CMV I.E. Promoter (*Proc. Natl. Acad. Sci.* (1984) 81:659–663) and the metallothionein promoter (*Nature* (1982) 296:39–42). Many additional promoters are known to persons of skill. The transcription cassettes comprise nucleic acids encoding the oligonucleotides of the invention.

Recombinant DNA techniques can be used to produce nucleocapsid polypeptides for use in the assays and compositions of the invention. In general, DNA encoding the nucleocapsid fragments of interest are cloned or isolated in a form suitable for ligation into an expression vector. After ligation, the vectors containing the DNA fragments or inserts are introduced into a suitable host cell for expression of recombinant nucleocapsid polypeptides. The polypeptides are then isolated from the host cells.

Once the nucleocapsid DNAs are isolated and cloned, one can express the desired polypeptides in a recombinantly engineered cell such as bacteria, yeast, insect, or mammalian cells. It is expected that those of skill in the art are knowledgeable in the numerous expression systems available for expression of the recombinantly produced proteins. No attempt to describe in detail the various methods known for the expression of proteins in prokaryotes or eukaryotes will be made.

In brief summary, the expression of natural or synthetic nucleic acids encoding nucleocapsid polypeptides will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the nucleocapsid polypeptides. To obtain high level expression of a cloned gene, it is desirable to construct expression plasmids which contain, at the minimum, a promoter to direct transcription, a ribosome binding site for translational initiation, and a transcription/translation terminator. See, Sambrook, Ausubel, and Berger, supra.

Transducing cells with nucleic acids can involve, for example, incubating the cells with viral vectors (e.g., retroviral or adeno-associated viral vectors) containing nucleic acids which encode inhibitors of interest. with cells within the host range of the vector. See, e.g., *Methods in Enzymiology*, vol. 185, Academic Press, Inc., San Diego, Calif. (D.V. Goeddel, ed.) (1990) or M. Krieger, *Gene Transfer and Expression-A Laboratory Manual*, Stockton Press, New York, N.Y., (1990) and the references cited therein. The culture of cells used in conjunction with the present invention, including cell lines and cultured cells from tissue or blood samples is well known in the art. Freshney (*Culture of Animal Cells, a Manual of Basic Technique, third edition* Wiley-Liss, New York (1994)) and the references cited therein provides a general guide to the culture of cells.

Illustrative of cell cultures useful for the production of targeted molecules include cells of insect or mammalian origin. Mammalian cell systems often will be in the form of monolayers of cells, although mammalian cell suspensions are also used. Illustrative examples of mammalian cell lines include monocytes, lymphocytes, macrophage, VERO and HeLa cells, Chinese hamster ovary (CHO) cell lines, WI38, BHK, 293 cells, Cos-7 or MDCK cell lines (see, e.g., Freshney, supra). Primary cultures of CD4+ and hematopoietic stem cells (CD34+) are also preferred.

As indicated above, the inhibitor, e.g., in the form of a plasmid which is used to transform a cell, preferably contains nucleic acid sequences to initiate transcription and sequences to control the translation of any polypeptide which is also encoded by the vector. These sequences are referred to generally as expression control sequences. When the host cell is of insect or mammalian origin, illustrative expression control sequences are obtained from Pol III t-RNA promoters (See, e.g., Wong-Staal et al. PCT/US94/05700) the SV-40 promoter (*Science* (1983) 222:524–527), HIV LTR promoters, the CMV I.E. Promoter (*Proc. Natl. Acad. Sci.* (1984) 81:659–663) or the metallothionein promoter (*Nature* (1982) 296:39–42). The cloning vector containing the expression control sequences is cleaved using restriction enzymes and adjusted in size as necessary or desirable and ligated with DNA coding for inhibitor by means well known in the art.

When higher animal host cells are employed, polyadenlyation or transcription terminator sequences from known mammalian genes are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al. (1983) *J. Virol.* 45: 773–781).

Additionally, gene sequences to control replication in a particular host cell are incorporated into the vector, such as those found in bovine papilloma virus type-vectors. See, Saveria-Campo (1985), "Bovine Papilloma virus DNA a Eukaryotic Cloning Vector" in *DNA Cloning Vol. II a Practical Approach* Glover (ed) IRL Press, Arlington, Va. pp. 213–238.

Host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, receptor-mediated endocytosis, electroporation and micro-injection of the DNA directly into the cells.

Transformed cells are cultured by means well known in the art. See, Freshny (supra), and Kuchler et al. (1977) *Biochemnical Methods in Cell Culture and Virology*, Kuchler, R. J., Dowden, Hutchinson and Ross, Inc. The expressed nucleic acids (and polypeptides, where appropriate) are isolated from cells grown as suspensions or as monolayers. The latter are recovered by well known mechanical, chemical or enzymatic means. See, Scopes, supra.

The inhibitors of the invention are most preferably cloned into gene therapy vectors derived from a retrovirus for transduction of cells in vitro. In these vectors, the inhibitors are placed into expression cassettes which direct expression of the active targeted molecules. Ideally, expression of the construct should be sufficiently high to inhibit the growth, infection or replication of the virus against which protection is sought. Accordingly, although the selection of a particular promoter is not a critical aspect of the invention, strong promoters are particularly preferred promoters for directing expression of the inhibitors in the cell. Preferred promoters include Pol III promoters such as the t-RNA promoters (e.g., the tRNAV$^{val}$ promoter; see, Wong-Staal et al. PCT/US94/05700), and strong basal promoters known to persons of skill, including cellular promoters, such as those which direct expression of the cytoskeletal machinery, such as the β-actin promoter and the tubulin promoter.

In addition to the constitutive promoters mentioned above, strong inducible promoters are also preferred. In particular, promoters which are expressed upon entry or replication of the virus in the cell are particularly preferred. For example, HIV LTR promoters are preferred promoters when the virus against which protection is sought is an HIV virus. Similarly, other retroviral LTR promoters (e.g., from any of the retroviruses or retroviral vectors herein) are also suitable, particularly when the targeted molecule is directed against the particular retrovirus.

Measuring Viral Inhibition

The level of virus in a cell culture, cell or whole organism is measured by means known in the art. Typically, the level of virus is measured in a western blot or other immunoassay such as an ELISA, or by performing quantitative PCR. In immunoassay formats, the level of virus is measured by monitoring the amount of a viral protein (or viral capsid, or capsid component) by quantifying binding of the protein to an immunogenic reagent such as an antibody. In quantitative PCR, the level of a viral nucleic acid is measured by monitoring PCR amplification products, and comparing the amount of amplified nucleic acid obtained, as compared to a amplification products obtained from amplification performed on a known reference nucleic acid.

Isolating Oligonucleotides Which Bind Nucleocapsid Protein with High Affinity

An oligonucleotide binds to a retroviral nucleocapsid protein (e.g., the HIV-1 NC protein, or HIV-1 Gag protein) with high affinity when it binds with a Kd of 0.01 μM or better. Typically, the high affinity oligoncleotides (and targeted molecules comprising high affinity oligonucleotide sequences) of the invention bind to the nucleocapsid protein with a Kd of about 0.01 μM to 1 pM. More preferably, the high affinity oligonucleotides bind with an affinity of about 10 to 0.1 nM or better. In many embodiments, high affinity molecules of the invention bind to NC proteins with an affinity of at least about 1 nM, generally at least about 0.1 nM, usually about 0.01 nM, and often higher. The precise affinity conditions will vary depending on the solvent. Example oligonucletoides include those which include the subsequences TGTGTG (SEQ ID NO:9), GACTTGTGGA (SEQ ID NO:10), and GACUUGUGG (SEQ ID NO:11), all of which bind to HIV-1 NC protein with affinities in the nanomolar range. Additional oligonucleotides which bind to NC proteins with high affinity can be determined by routine screening. In the screening assays of the invention, an oligonucleotide is screened for binding properties to nucleocapsid protein. The example oligonucleotides can be used as positive controls for comparison to a nucleotide to be tested in the screening assays.

Many screening formats are desirable, appropriate, and well-known for monitoring the interaction between nucleic acid binding proteins and nucleic acids, and these techniques are applicable to monitoring the interaction between nucleocapsid proteins and oligonucleotides. Typically, the assays include nucleocapsid protein and a target oligonucleotide, and the Kd of the oligonucleotide-protein interaction determined. Either the oligonucleotide or the nucleocapsid protein can be labeled. Appropriate screening assays include gel-retardation assays, footprinting assays, capillary zone electrophoresis, NMR, surface plasmon resonance, and changes in intrinsic fluorescence of aromatic residues on the nucleocapsid protein.

Assays for Measuring Oligonucleotide and Targeted Molecule Binding to nucleocapsid The invention provides assays for monitoring oligonucleotide and targeted molecule binding to retroviral nucleocapsid proteins, including Gag and NC. In the assays of the invention, the oligonucleotide or targeted molecule ("trial compound") is incubated with the retroviral nucleocapsid protein, and changes in the physical or chemical properties over time are monitored. In most assay formats, either protein or trial compound properties can be monitored. Appropriate assays include gel-retardation assays, footprinting assays, capillary zone electrophoresis, NMR, plasmon resonance, and changes in intrinsic fluorescence of aromatic residues on the nucleocapsid protein. Similarly, the inhibition or facilitation of binding of an oligonucleotide to an NC by a "target" or "test" compound can be monitored. Compounds which inhibit binding of an oligonucleotide to an NC protein are candidate inhibitors of NC protein action (i.e., because the inhibitors inhibit the binding of NC to nucleic acids during viral assembly or in other phases of the viral life cycle). Assays which identify potential inhibitors of NC proteins are of immediate commercial value to pharmaceutical companies for the identification of potential anti-viral therapeutics.

In a preferred embodiment, the assay format is surface plasmon resonance (SPR). The Kd and kinetics of the trial compound-protein interaction are determined in a BIAcore, a biosensor based on surface plasmon resonance. For this technique, protein or trial compound is coupled to a derivatized sensor chip capable of detecting changes in mass. When trial compound or protein is passed over the sensor chip, it binds to the trial compound or protein coupled to the chip, resulting in an increase in mass which is quantifiable. Measurement of the rate of association as a function of trial compound or protein concentration can be used to calculate the association rate constant (kon). After the association phase, buffer is passed over the chip and the rate of dissociation (koff) is determined. Kon is typically measured in the range $1.0 \times 10^2$ to $5.0 \times 10^6$ and koff in the range $1.0 \times 10^{-1}$ to $1.0 \times 10^{-6}$. The equilibrium constant Kd is often calculated as koff/kon and thus is typically measured in the range $10^{-5}$ to $10^{-12}$. Affinities measured in this manner correlate well with affinities measured in solution by fluorescence quench titration. See, Fisher and Fivash (1994) Curr. Opin. Biotechnol. 5:389–395; Fisher et al. (1994) Methods 6:389–395; Johnsson et al., (1991) Anal. Biochem., 198:268–277; Karlsson et al., (1991) J. Immunol. Methods., 145:229–240; and Johnsson et al., (1991) Anal. Biochem. 198:268–277.

A kit incorporating the plasmon resonance assay can be used to identify and study compounds which interfere with retroviral nucleocapsid binding to a trial compound, or to identify compounds which bind to retroviral nucleocapsid proteins. Such a kit would contain, one or more of: instructions, purified concentrated retroviral nucleocapsid protein, an oligonucleotide (or compound comprising an oligonucleotide) which binds the retroviral nucleocapsid protein, related reagents and the like.

Changes in electrophoretic mobility of the protein or trial compound upon binding can be detected by the standard technique of capillary zone electrophoresis (CZE). For a general description of CZE, see, e.g., Capillary Electrophoresis, Theory and Practice (Academic Press, Inc. Grossman and Colburn (eds.) (1992)), which is incorporated herein by reference. Generally, electrophoretic mobility of the protein or trial compound (at a pH determined by the buffer in the capillary electrophoresis tube) is used to move the retroviral nucleocapsid protein from a fixed starting position towards one electrode. The migration rate may be monitored by UV absorption, e.g., at 215 nm where the protein is monitored. Sample tubes containing an appropriate amount of a solution comprising the retroviral nucleocapsid protein of choice, with and without the compound to be tested for nucleocapsid binding are placed in an automatic sample injector. At programmed intervals, samples are drawn into the capillary tube and the UV absorption is monitored. Unmodified retroviral nucleocapsid protein gives a sharp peak of migrating protein passing the detector. Modifications of the protein, caused by binding the trial compound of choice, are revealed by a change in the electrophoretic mobility of the reacted protein.

Capillary zone electrophoresis has the advantage of simple automation, since many different samples can be loaded and analyzed in successive runs. Each run requires about 10 minutes and each sample tube can be analyzed multiple times. An example of a kit utilizing CZE for analysis of selected compounds to be tested for nucleocapsid binding would contain about 100 micrograms ($\mu$g) of purified retroviral nucleocapsid protein, typically complexed with zinc in, for example, 1.0 ml of water, and could be used for the testing of approximately 1000 trial compounds. A kit would optionally comprise instructions, packaging materials, buffers, control high affinity oligonucleotides and the like.

Gel mobility shift assays are routinely used for detecting nucleic acid-protein binding. Typically, the nucleic acid is labeled, e.g., using $^{32}$P and a kinase enzyme. The nucleic acid is incubated with a protein in the presence of non-specific competitors (poly d(I-C), heparin, salmon sperm DNA, or other polyionic molecules). The nucleic acid and protein are then electrophoresed through a non-denaturing gel. A shift in the mobility of the labeled nucleic acid indicates binding of the labeled nucleic acid to the protein. In the present invention, the protein is a retroviral nucleocapsid protein, and the labeled nucleic acid comprises a sequence which binds to nucleocapsid protein with high affinity. Essentially any nucleic acid, compound comprising a nucleic acid, or mixture of nucleic acids can be tested for binding to retroviral nucleocapsid protein by this method. In addition, a wide variety of compounds can be tested for their effect on nucleic acid-protein binding.

A kit incorporating the gel-mobility shift assay can be used to identify and study compounds which interfere with retroviral nucleocapsid binding to an oligonucleotide, or to identify oligonucleotides which bind to retroviral nucleocapsid proteins. Such a kit would contain, one or more of: purified concentrated retroviral nucleocapsid protein, an oligonucleotide which binds the retroviral nucleocapsid protein, and appropriate size standards to monitor the change in mobility through the gel due to nucleic acid binding.

Changes in the intrinsic fluorescence of aromatic protein moieties are commonly used to monitor a reaction which involves a change in protein conformation. In the present invention, fluorescence can be used to monitor the binding of compounds to retroviral nucleocapsid proteins. The intrinsic fluorescence of Trp-37 in the second zinc finger of HIV-1 nucleocapsid protein has been used to monitor nucleic acid binding and conformation of the zinc finger complex (see, Summers, et al., *Protein Science* 1:563 (1992)).

NMR can be used to monitor binding to retroviral nucleocapsid proteins (see, e.g., Rice, et al., *Nature* 361:473–475 (1993)). It is expected that one of skill is familiar with the general technique of NMR and its many applications to monitor protein-ligand interactions. Briefly, the atoms in retroviral nucleocapsid proteins bound to a nucleic acid share a different local environment than nucleocapsid proteins which are not similarly bound. The difference in local environment leads to distinct NMR spectra for protein molecules which bind nucleic acid, versus those that do not. By monitoring, for example, the proton ($^1$H) spectrum of a sample containing nucleic acid-bound retroviral nucleocapsid protein, and a compound of the present invention over time, it is possible to measure binding of the compound to the protein.

Since NMR can be used to provide the percent of protein molecules which are bound over time, it is also possible to use this technique to define the reaction kinetics of a given reaction. Similarly, NMR may be used to monitor the effect of trial compounds upon the binding of nucleocapsid proteins to nucleic acid complexes. Kits containing eg., purified retroviral nucleocapsid proteins and oligonucleotides which bind nucleocapsid proteins may be used to standardize the practice of this method.

Artificial fluorescent probes can also be incorporated into a protein to provide for the detection of changes in conformation. Poly ethino-adenine, for example, has been used as a fluorescent nucleotide to measure the extent of nucleocapsid protein binding (see, Karpel, et al., *J. Biol. Chem* 262, 4961 (1987)).

Methods of placing assay components into arrays and performing parallel analysis of the arrayed components are also known and available. See, Pirrung et al., U.S. Pat. No. 5,143,854 (see also PCT Application No. WO 90/15070), McGall et al., U.S. Pat. No. 5,412,087, Chee et al. SN PCT/US94/12305, Fodor et al., PCT Publication No. WO 92/10092; Fodor et al. (1991) *Science*, 251: 767–777; Lipshutz et al. (1995) *BioTechniques* 19(3): 442–447; Fodor et al. (1993) *Nature* 364: 555–556; and Medlin (1995) *Environmental Health Perspectives* 244–246.

Sample preparation steps for analysis in the assays described herein are conveniently performed in parallel. For example, a selected sample of nucleocapsid protein can be simultaneously mixed in separate reactions with several trial compounds. Alternatively, a single trial compound can be separately mixed with several different nucleocapsid protein types (e.g., NC and/or Gag protein derived from different species or isolates of retrovirus). Mixing is conveniently performed in multi-well plates such as standard 96 well microtiter plates.

The assays above determine the interaction of a trial compound and a retroviral nucleocapsid protein. Any of the above assays are used in a competitive or non-competitive format to determine the effect of a test compound on the binding of a retroviral nucleocapsid protein to any selected trial compound. In this embodiment, the test compound is optionally added before or during the binding of the trial compound to the retroviral nucleocapsid protein. The effect of the test compound on trial compound binding is then determined, typically by comparison to a control assay which measures the binding of the trial compound to the retroviral nucleocapsid protein in the absence of the test compound.

The trial compound comprises an oligonucleotide sequence which binds to the retroviral nucleocapsid protein (in one class of preferred embodiments, the trial compound is an oligonucleotide which binds to a nucleocapsid protein with high affinity). The test compound can be essentially any compound. The test and trial compound are added simultaneously to the retroviral nucleocapsid protein, or the test compound can be added to the nucleocapsid protein before or after addition of the trial compound. As described above, the binding of the trial compound to the retroviral nucleocapsid protein is monitored over time. Test compounds which inhibit binding of trial compounds to retroviral nucleocapsid proteins are used to inhibit binding of retroviral nucleocapsid proteins to retroviral RNA, thereby inhibiting retroviral replication. Such assays are of considerable value to pharmaceutical and drug discovery companies for the identification of test compounds which inhibit binding of retroviral nucleocapsid proteins to retroviral RNA. Kits for practicing the assays can be made. The kits will typically include one or more of the following: a container, directions for practicing the assay, oligonucleotides which bind retroviral nucleocapsid proteins, buffers, purified retroviral nucleocapsid proteins, components to be used with the assay equipment (gel columns, NMR sample tubes, BIAcore chips, etc.) and the like.

Use of the Oligonucleotides of the Invention to Purify and Detect Retroviral Nucleocapsid Protein In one embodiment, the present invention provides convenient materials for the purification of NC or Gag protein. In particular, compounds which comprise the oligonucleotides of the invention are used in affinity columns for the purification of NC or Gag. The affinity columns have a matrix which includes the oligonucleotides of the invention. When the Gag or NC proteins are passed over the matrix, they bind to the oligonucleotides in the matrix. Unwanted materials are washed from the column with a low salt buffer. The Gag or NC proteins are then washed from the column with higher salt buffers. Methods for making and using oligonucleotide affinity columns are known to those in the art.

In one embodiment, the oligonucleotides of the invention (or targeted molecules comprising the oligonucleotides of the invention) which bind to NC are used as molecular probes for the detection of NC proteins. Typically, a protein sample containing NC protein is electrophoresed through a non-denaturing gel and blotted onto a substrate. Labeled oligonucleotide is then added to the substrate, and binding is monitored. Many assays for the detection of nucleic acid-binding proteins using labeled nucleic acids are known and are applicable to the present invention, including southwestern blots, Northwestern blots, gel-mobility shift assays, and the assays described herein.

Detection of retroviral nucleocapsid protein is an indication of viral infection of cells in a biological sample; accordingly, detection of the proteins are a diagnostic indicator of viral infection.

As described, the oligonucleotides which specifically bond to an NC protein are used for detection and/or purification of the NC protein. Detection methods of the invention provide significant advantages over present methods for the detection of, e.g., HIV infection. In present methods, HIV (or other retroviruses) is commonly detected by monitoring patient blood for the presence of antibodies against HIV. This indirect method of detecting HIV is subject to false-positive signals from cross reactive antibodies, and further suffers from the limitation that the immune response necessary for formation of anti-HIV antibodies can take several months—causing HIV infection to go undetected for the first several months of infection.

In contrast, in the methods of the invention, oligonucleotides which specifically bind NC proteins are used for the direct detection of HIV (or other retroviral) NC components, including NC, Gag precursor proteins and intact or partially intact virus. Because the presence of the virus is detected directly, it is possible to detect infection in early stages, before antibodies to the virus are formed. Accordingly, the present invention is particularly useful for early detection of viral infection. Similarly, in purification embodiments, an oligonucleotide is used as a molecular tag for the purification of the retroviral NC protein, e.g., as an affinity tag.

Many additional detection and purification formats are suitable. In detection aspects, the NC specific oligonucleotide will ordinarily comprise a detectable label. The particular label or detectable group used in the assay is not a critical aspect of the invention, so long as it does not significantly interfere with the specific binding of the oligonucleotide to the NC protein. The detectable group can be any material having a detectable physical or chemical property. Such detectable labels have been well-developed and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e. g., $^3$H, $^{125}$I, $^{35}$S, $^{14}$C, $^{32}$P, or $^{33}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads. The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions. Linkers are suitably added to NC specific oligonucleotides for attachment to labels or purification components (magnetic beads comprising specific NC oligonucleotides, affinity columns made with such nucleotides, etc.)

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, oligonucleotide -coated particles are agglutinated by samples comprising the target NC proteins. In this format, none of the components need be labeled and the presence of the target NC protein is detected by simple visual inspection.

As mentioned above, depending upon the assay, various components, including the oligonucleotide, NC proteins, or components which bind either of these, is optionally bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass, plastic or magnetic bead. The desired component may be covalently bound or non-covalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, are included substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

Thus, a variety of detection and purification methods are suitable. Particularly preferred purification methods include coating magnetic beads with NC-specific oligonucleotides for the purification of NC proteins, e.g., from human blood (e.g., HIV NC components) and affinity columns with NC-specific oligonucleotides.

Targeted Molecules

In another aspect, the present invention provides a targeted molecule which binds to a retroviral NC protein with high affinity, the targeted molecule comprising an oligonucleotide and a fusion partner. The oligonucleotide used in the targeted molecules of the present invention can be any oligonucleotide which binds to a retroviral NC protein with high affinity. Such oligonucleotides include, but are not limited to, oligonucleotides comprising a sequence selected from the group consisting of TGTGTG (SEQ ID NO:9), GACTTGTGGA (SEQ ID NO:10) and GACUUGUGG (SEQ ID NO:11). In a presently preferred embodiment, the oligonucleotide binds to HIV-1 with high affinity. In another preferred embodiment, the oligonucleotide comprises the sequence TGTGTG (SEQ ID NO:9). In another preferred embodiment, the oligonucleotide comprises the sequence GACTTGTGGA (SEQ ID NO:10). In an equally preferred embodiment, the oligonucleotide comprises the sequence GACUUGUGG (SEQ ID NO:11).

In the targeted molecules of the present invention, the fusion partner can be any of a variety of atoms or molecules, including, but not limited to, peptides, proteins, antibodies, toxins, enzymes, cofactors, drugs, labels, etc. In a presently preferred embodiment, the fusion partner chemically reacts with the retroviral NC protein (including the Gag precursor), thereby reducing the ability of the NC protein to package retroviral RNA. As such, any molecule which can react with the retroviral NC protein and, in turn, reduce its ability to package retroviral RNA can be used as the fusion partner in the targeted molecules of the present invention.

In a preferred embodiment, the fusion partner is cytotoxic. In another preferred embodiment, the fusion partner is a protein. In a further preferred embodiment, the fusion partner is a compound which can be used to inactivate retroviruses, such as HIV-1, by attacking the CCHC zinc fingers of the viral nucleocapsid protein and ejecting the zinc therefrom. Several classes of such compounds are disclosed in co-pending, commonly assigned U.S. Pat. application Ser. No. 08/379,420, filed Jan. 27, 1995, the teachings of which are incorporated herein by reference for all purposes. More particularly, the classes of such compounds include, but are not limited to, the following:

disulfides having the formula

maleimides having the formula

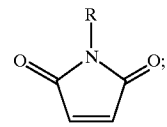

α-halogenated ketones having the formula

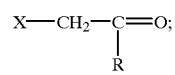

nitric oxide and derivatives containing the NO group;
hydrazides having the formula R—NH—NH—R;
nitroso compounds having the formula R—NO;

cupric ions and complexes containing $Cu^{+2}$;
ferric ions and complexes containing $Fe^{+3}$; and
alkylating agents;
wherein R can be any atom or molecule, and X is a halogen selected from the group consisting of I, F, Br and Cl.

Preferred R groups include, for example, alkyl groups (branched or unbranched, saturated or unsaturated, including monovalent hydrocarbon radicals with from 1–12 carbons); substituted alkyls (an alkyl having one or more functional group such as a lower alkyl, aryl, acyl, halogen (i.e., alkylhalos, e.g., CF3), hydroxy, amino, alkoxy, alkylamino, acylamino, acyloxy, aryloxy, aryloxyalkyl, mercapto, both saturated and unsaturated cyclic hydrocarbons, heterocycles and the like); aryls (aromatic substituents such as single or multiple aromatic rings which are fused together, linked covalently, or linked to a common group such as a methylene or ethylene moiety); aromatic ring(s) including phenyl, naphthyl, biphenyl, diphenylmethyl and benzophenone among others. Similarly, substituted aryls, including an aryl and including one or more functional group such as a lower alkyl, acyl, halogen, alkylhalos, hydroxy, amino, alkoxy, alkylamino, acylamino, acyloxy, mercapto and both saturated and unsaturated cyclic hydrocarbons which are fused to an aromatic ring(s), linked covalently or linked to a common group such as a methylene or ethylene moiety are also preferred. Acyl groups with ketone substituents, —C(O)R, where R is alkyl or substituted alkyl, aryl or substituted aryl are often suitable. Halogens, including fluorine, bromine, chlorine and iodine atoms are contemplated. Hydroxy groups (OH), primary amines (R—NH2) or Alkoxy groups (an —OR group, where R is a lower alkyl, substituted lower alkyl, aryl, substituted aryl, arylalkyl or substituted arylalkyl can be used, and are substituted for one another. Alkylamino groups are used including secondary and tertiary amines wherein the alkyl groups may be either the same or different and may consist of straight or branched, saturated or unsaturated hydrocarbons. Mercapto groups having the general structure R—S—R' wherein R and R' are the same or different and are alkyl, aryl or heterocyclic as described herein are optionally used to provide a separate reactive site, as are any of the primary chemically reactive groups indicated herein. Saturated cyclic hydrocarbons such as cyclopropyl, cyclobutyl, cyclopentyl, etc., and substituted analogues of these structures are optionally substituted for one another in the targeted molecules of the invention. Unsaturated cyclic hydrocarbons (a monovalent non-aromatic group with at least one double bond, such as cyclopentene, cyclohexene, etc. and substituted analogues thereof are optionally substituted for one another in the targeted molecules of the invention. Heteroaryl groups having aromatic rings in which one or more carbon atoms of the aromatic ring(s) are substituted by a heteroatom such as nitrogen, oxygen or sulfur with a single aromatic ring, multiple aromatic ring(s), or one or more aromatic rings coupled to one or more non-aromatic ring(s) can be substituted for one another using standard organic chemical synthetic methods. In structures having multiple rings, the rings can be fused together, linked covalently, or linked to a common group such as a methylene or ethylene moiety. Substituted Heteroaryl groups having one or more functional group such as lower alkyl, acyl, halogen, alkylhalos (e.g. CF3), hydroxy, amino, alkoxy, alkylamino, acylamino, acyloxy, mercapto, etc. are optionally substituted for one another. Heterocyclic groups having a monovalent saturated or unsaturated non-aromatic group having a single ring or multiple condensed rings from 1–12 carbon atoms and from 1–4 heteroatoms selected from nitrogen, sulfur or oxygen within the ring are optionally used and are optionally substituted for one another. All of these compounds are made using standard synthetic techniques, and it will be appreciated that many conservatively substituted (i.e., by substituting the example compounds herein with groups having similar functionality as described) are commercially available.

Examples of suitable disulfide compounds which can be used in the targeted molecules of the invention include, but are not limited to, tetramethylthiuram disulfide, tetrethylthiuram disulfide, tetraisopropylthiuram disulfide, tetrabutylthiuram disulfide, dicyclopentamethylenethiuram disulfide, isopropylxanthic disulfide, 0,0-diethyl dithiobis-(thioformate), benzoyl disulfide, benzoylmethyl disulfide, formamidine disulfide 2HCl, 2-(diethylamino)ethyl disulfide, aldrithiol-2, aldrithiol-4, 2,2-dithiobis(pyridine n-oxide), 6,6-dithiodinicotinic acid, 4-methyl-2-quinolyl disulfide, 2-quinolyl disulfide, 2,2-dithiobis(benzothiazole), 2,2-dithiobix(4-tert-butyl-1-isopropyl)-Imidazole, 4-(dimethylamino)phenyl disulfide, 2-acetamidophenyl disulfide, 2,3-dimethoxyphenyl disulfide, 4-acetamidophenyl disulfide, 2-ethoxycarboxamido)phenyl disulfide, 3-nitrophenyl disulfide, 4-nitrophenyl disulfide, 2-aminophenyl disulfide, 2,2-dithiobix(benzonitrile), p-Tolyl disulfoxide, 2,4,5-trichlorophenyl disulfide, 4-methylsulfonyl-2-nitrophenyl disulfide, 4-methylsulfonyl-2-nitrophenyl disulfide, 3,3-dithiodipropionic acid, n,n-diformyl-cystine, Trans-1,2-dithiane-4,5-diol, 2-chloro-5-nitrophenyl disulfide, 2-amino-4-chlorophenyl disulfide, 5,5-dithiobis(2-nitrobenzoic acid), 2,2-dithiobix(1-naphtylamine), 2,4-dinitrophenyl p-Tolyl disulfide, 4-nitrophenyl p-Tolyl disulfide, and 4-chloro-3-nitrophenyl disulfideformamidine disulfide dihydrochloride. A wide variety of other suitable disulfides suitable for coupling to an oligonucleotide of the invention are found in Rice et al. (1996) *J. Med. Chem* 39:3606, where a variety of disulfide compounds are shown to inhibit retroviral replication. These include aromatic disulfides, aliphatic disulfides, nonsymetrical disulfides, thiuram disulfides, aromatic disulfoxides, aromatic disulfones, aromatic thiosulfones and nonaromatic thiosulfones. See also, Rice and Turpin (1996) *Medical Virology* 6:187–199 for a discussion of the chemical mechanism of attack for various compounds on the zinc finger nucleocapsid protein.

An example of a maleimide is n-ethylmaleimide. An example of a hydrazide is 2-(carbamoylthio)-acetic acid 2-phenylhydrazide. Examples of suitable alkylating agents which can be used in the targeted molecules of the invention include, but are not limited N-ethylmaleimide and N-hydroxyl succinimide. An example of a suitable hydrazide which can be used in the targeted molecules of the invention is 2-(carbamoylthio)-acetic acid 2-phenylhydrazide.

C-Nitroso compounds have been shown to attack the zinc finger of NC. Incubation of HIV-1 with the C-nitroso compound 3- nitroso benzamide (NOBA) results in loss of zinc from a synthetic peptide with a HIV-1 CCHC (SEQ ID NO:2) zinc finger and in viral inactivation (Rice et al. (1993) *Nature* 361, 473). Removal of zinc from the eukaryotic CCHC (SEQ ID NO:2) zinc finger of poly(ADP-ribose) polymerase by C-nitroso compounds has been reported (Buki et al. (1991) *FEBS Letters* 290, 181). Accordingly, C-nitroso compounds are also chemically coupled to the oligonucleotides of the invention to chemically inactivate NC proteins.

In forming the targeted molecules of the present invention, the oligonucleotide is preferably chemically conjugated or coupled to the fusion partner. Means of chemically conjugating molecules are known to and used by those of skill in the art (see, March, *Advanced Organic Chlemistry*, 4th Ed., Wiley-Interscience, New York, N.Y., 1992, the teachings of which are incorporated herein by reference).

The particular procedure used for attaching the oligonucleotide to the fusion protein will vary depending on the chemical nature of both the oligonucleotide and the fusion partner. Most of the fusion partners set forth above will contain a variety of functional groups which are available for reaction with a suitable functional group on the oligonucleotide. Such functional groups include, but are not limited to, carboxyl groups, amino groups, hydroxyl groups, thiol groups and the like.

In another embodiment, the oligonucleotide or the fusion partner can be derivatized to attach additional reactive functional groups. The derivatization optionally involves attachment of linker molecules such as those available from Pierce Chemical Company, Rockford Illinois. A "linker", as used herein, is a molecule that is used to join the fusion partner to the oligonucleotide. The linker is capable of forming covalent bonds to both the fusion partner and the oligonucleotide. Suitable linkers are well known to those of skill in the art and include, but are not limited to, straight or branched-chain carbon linkers, heterocyclic carbon linkers or peptide linkers. In addition, a bifunctional linker having one functional group reactive with the fusion partner, and another functional group reactive with the oligonucleotide, can be used to form the desired targeted molecules. Alternatively, derivatization can proceed through chemical treatment of the fusion partner or oligonucleotide. For example, glycol cleavage of the sugar moiety of a glycoprotein with periodate can generate free aldehyde groups which, in turn, can be reacted with free amine or hydrazine groups on an agent to bind the agent thereto (See, e.g., U.S. Pat. No. 4,671,958). Procedures for generation of free sulfhydryl groups on polypeptides are known (See, e.g., U.S. Pat. No. 4,659,839). Moreover, many procedures and linker molecules for attachment of various compounds to proteins are known. See, for example, European Patent Application No. 188,256; U.S. Pat. Nos. 4,671,958, 4,659,839, 4,414, 148, 4,699,784; 4,680,338; 4,569,789; and 4,589,071; and Borlinghaus et al. *Cancer Res.* 47: 4071–4075 (1987).

Alternatively, the oligonucleotide can be functionalized at the 3'- or 5'-terminus to introduce a functional group which, in turn, is reactive with a functional group of the fusion partner of interest. The functionalization typically involves reacting the oligonucleotide with, for example, a 3'-modifier or a 5'modifier such as those which are commercially available from Glen Research. For instance, the Glen Research 3'-amino-modifier CPGs are designed to functionalize the 3'-terminus of the oligonucleotide of interest by the introduction of a primary amine, whereas the 3'-thiol-modifier is used to introduce a 3'-thiol linkage in an oligonucleotide. Similarly, the Glen Research 5'-amino-modifiers are designed to functionalize the 5'-terminus of the oligonucleotide of interest by the introduction of a primary amine, whereas the 5'-thiol-modifier is used to introduce a 5'-thiol linkage in an oligonucleotide. Glen Research provides numerous modifiers which can be used to functionalize the oligonucleotides used in the targeted molecules of the present invention. Such modifiers include, but are not limited to, 3'-amino-modifier C3 CPG 500, 3'-amino-modifier C7 CPG 500, 3'-thiol-modifier C3 S-S CPG 500, glyceryl CPG 500, 5'-amino-modifier C3, 5'-amino-modifier C6, 5'amino-modifier C6-TFA, 5'-amino-modifier C12, 5'-thiol-modifier C6, 5'-amino-modifier 5, thiol-modifier C6 S-S, etc. In addition, Glen Research supplies a *User Guide To DNA Modification And Labelling* which describes the use of the various modifiers, the teachings of which are incorporated herein by reference. Once the oligonucleotide is appropriately functionalized, the fusion partner can be covalently attached to the oligonucleotide, for example, by means of an ether, ester, carbamate, phosphate ester or amine linkage. Methods of forming ether, ester, carbamate, phosphate ester and amide linkages are known to those of skill in the art and, in addition, particular reagents and references which can be used to form such linkages can be found in such texts as March, *Advanced Organic Chemistry*, 4th Ed., Wiley-Interscience, New York, N.Y., 1992, incorporated herein by reference. In addition to chemical moieties, other functional groups such as peptides, proteins, nucleic acids and the like are attached to the oligonuclotide through the appropriate chemical linkage (e.g., an amino or carboxyl linkage for a polypeptide).

Preferred protein fusion partners include antibodies and antibody fragments which can bind to NC or secondary molecules such as cellular proteins, thereby sterically inhibiting the activity of the NC protein, peptidases which cleave the NC protein, anti-sense or ribozyme molecules which sterically inhibit the activity of the NC protein, or which cleave nucleic acids bound by the NC protein (such as a viral transcript), thereby altering the activity of the NC protein. Ribozyme or anti-sense molecules are optionally recombinantly encoded with the oligonucleotide component of the targeted molecule, e.g., in a vector which is expressed in a cell infected by a retrovirus such as HIV.

Polypeptides are made using standard synthetic or recombinant techniques as described, e.g., in Ausubel, Sambrook and Berger, supra., and in Scopes (1982) *Protein Purification: Principles and Practice* Springer-Verlag New York. Antibodies exist, for example, as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the F(ab)'2 dimer into an Fab' monomer. The Fab' monomer is essentially an Fab with part of the hinge region (see, Fundamental Immunology, Third Edition, W. E. Paul, ed., Raven Press, N.Y. (1993), which is incorporated herein by reference, for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies. Methods of producing polyclonal and monoclonal antibodies are known to those of skill in the art, and many anti-viral antibodies are commercially available. See also, e.g., Coligan (1991) *Current Protocols in Immunology* Wiley/Greene, New York; and Harlow and Lane (1989) *Antibodies: A Laboratory Manual* Cold Spring Harbor Press, New York; Stites et al. (eds.) *Basic and Clinical Immunology* (4th ed.) Lange Medical Publications, Los Altos, Calif., and references cited therein; Goding (1986) Monoclonal Antibodies: Principles and Practice (2d ed.) Academic Press, New York, N.Y.; and Kohler and Milstein (1975) Nature 256: 495–497. Such techniques include antibody preparation by selection of antibodies from libraries of recombinant antibodies in phage or similar vectors. See, Huse et al. (1989) *Science* 246: 1275–1281; and Ward, et al. (1989) *Nature* 341: 544–546. Specific monoclonal and polyclonal antibodies and antisera will usually bind with a $K_D$ of at least about 0.1 µM, preferably at least about 0.01 µM or better, and most typically and preferably, 0.001 µM or better.

Cellular Transformation and Gene Therapy

The present invention provides nucleic acids which encode oligonucleotides with a high affinity for retroviral nucleocapsid proteins such as an HIV NC or Gag protein. A nucleocapsid decoy oligonucleotide is an oligonucleotide having a sequence bound by a retroviral nucleocapsid protein. Upon expression in a cell, the decoy nucleic acid binds to any available nucleocapsid protein (including the Gag precursor), thereby blocking the binding of the nucleocapsid protein to retroviral RNA, and preventing packaging of the RNA. Blocking packaging results in reduced virus formation, thereby inhibiting retroviral replication.

In one particularly preferred class of embodiments, the nucleic acids of the invention are used in cell transformation procedures for gene therapy. Gene therapy provides methods for combating chronic infectious diseases, such as HIV, as well as non-infectious diseases such as cancer and birth defects such as enzyme deficiencies. For example, Yu et al. (1994) *Gene Therapy* 1:13–26 and the references therein provide a general guide to gene therapy strategies for HIV infection. See also, Sodoski et al. PCT/US91/04335. In addition to ex vivo procedures, gene therapy vectors, such as retroviral, or AAV vectors encoding a molecular decoy of the invention, can be administered directly to the organism for transduction of cells in vivo.

Several approaches for introducing nucleic acids into cells in vivo, ex vivo and in vitro have been used. These include liposome based gene delivery (Debs and Zhu (1993) WO 93/24640; Mannino and Gould-Fogerite (1988) *BioTechniques* 6(7): 682–691; Rose U.S. Pat. No. 5,279,833; Brigham (1991) WO 91/06309; and Felgner et al. (1987) *Proc. Natl. Acad. Sci. USA* 84: 7413–7414) and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4:43, and Cornetta et al. *Hum. Gene Ther.* 2:215 (1991)).

The transcription cassettes of the invention, which encode oligonucleotides which bind to nucleocapsid protein with high affinity, are typically cloned into gene therapy vectors that are competent to transform cells in vitro and/or in vivo. For a review of gene therapy procedures, see, Anderson, *Science* (1992) 256:808–813; Nabel and Felgner (1993) TIBTECH 11: 211–217; Mitani and Caskey (1993) TIBTECH 11: 162–166; Mulligan (1993) *Science* 926–932; Dillon (1993) TIBTECH 11: 167–175; Miller (1992) *Nature* 357: 455–460; Van Brunt (1988) *Biotechnology* 6(10): 1149–1154; Vigne (1995) *Restorative Neurology and Neuroscience* 8: 35–36; Kremer and Perricaudet (1995) *British Medical Bulletin* 51(1) 31–44; Haddada et al. (1995) in *Current Topics in Microbiology and Immunology* Doerfler and Bohm (eds) Springer-Verlag, Heidelberg Germany; and Yu et al., *Gene Therapy* (1994) 1:13–26.

Widely used retroviral vectors include those based upon murine leukemia virus (MuLV), gibbon ape leukemia virus (GaLV), Simian Immnuno deficiency virus (SIV), human immuno deficiency virus (HIV), and combinations thereof. See, e.g., Buchscher et al. (1992) *J. Virol.* 66(5) 2731–2739; Johann et al. (1992) *J. Virol.* 66 (5):1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology, Third Edition* Paul (ed) Raven Press, Ltd., New York and the references therein, and Yu et al., *Gene Therapy* (1994) supra).

AAV-based vectors are also used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 and Samulski (supra) for an overview of AAV vectors. Construction of recombinant AAV vectors are described in a number of publications, including Lebkowski, U.S. Pat. No. 5,173, 414; Tratschin et al. (1985) *Mol. Cell. Biol.* 5(11) :3251–3260; Tratschin, et al. (1984) *Mol. Cell. Biol.*, 4:2072–2081; Hermonat and Muzyczka (1984) *Proc. Natl. Acad. Sci. USA*, 81:6466–6470; McLaughlin et al. (1988) and Samulski et al. (1989) *J. Virol.*, 63:03822–3828. Cell lines that can be transformed by rAAV include those described in Lebkowski et al. (1988) *Mol. Cell. Biol.*, 8:3988–3996.

Ex vivo methods for inhibiting viral replication in a cell in an Iorganism involve transducing the cell ex vivo with a nucleic acid of this invention which expresses a nucleocapsid oligonucleotide molecular decoy of the invention, and introducing the cell into the organism. The cells are typically CD4+ cells, such as CD4+ T cells, or macrophage isolated or cultured from a patient, or stem cells. The culture of cells used in conjunction with the present invention, including cell lines and cultured cells from tissue or blood samples is well known in the art. Freshney (*Culture of Animal Cells, a Manual of Basic Technique, third edition* Wiley-Liss, New York (1994)) and the references cited therein provides a general guide to the culture of cells. Transformed cells are cultured by means well known in the art. See, also Kuchler et al. (1977) *Biochemical Methods in Cell Culture and Virology*, Kuchler, R. J., Dowden, Hutchinson and Ross, Inc. Mammalian cell systems often will be in the form of monolayers of cells, although mammalian cell suspensions are also used. Alternatively, cells can be derived from those stored in a cell bank (e.g., a blood bank).

In one preferred use of the invention, expression of an oligonucleotide molecular decoy inhibits retroviral replication (e.g., HIV replication) in any of those cells already infected with the retrovirus, in addition to conferring a protective effect to cells which are not infected by the retrovirus. Thus, an organism infected with a retrovirus can be treated for the infection by transducing a population of its cells with a vector of the invention and introducing the transduced cells back into the organism as described herein. Thus, the present invention provides a method of protecting cells in vitro, ex vivo or in vivo, even when the cells are already infected with the virus against which protection is sought.

In one particularly preferred embodiment, stem cells (which are typically CD34+, and not typically CD4+) are used in ex-vivo procedures for cell transformation and gene therapy to inhibit viral replication in immune cells such as T-cells. For example, HIV replication can be inhibited by transforming stem cells with the nucleic acids of the invention. The advantage to using stem cells is that they can be differentiated into other cell types in vitro, or can be introduced into a mammal (such as the donor of the cells) where they will engraft in the bone marrow.

Hematopoietic stem cells are particularly preferred targets for cell transformation in general, and for gene therapy (particularly anti-HIV gene therapy) in particular. HIV-based retroviral vectors comprising a transcription cassette encoding an oligonucleotide molecular decoy of the invention are made competent to transform CD34+ cells by pseudotyping the HIV-based vector. This is done by transducing the packaging cell line used to package the retroviral vector with a nucleic acid which encodes the vesicular stomatitis virus (VSV) envelope protein, which is then expressed on the surface of the retroviral vector. VSV infects both dividing and non-dividing CD34+ cells, and pseudotype vectors expressing VSV envelope proteins are competent to transduce these cells. See, Naldini et al. (1996) *Science* 272:263. Other HIV vector systems are also available, and adaptable to use in the present invetion, e.g., for pseudotyping. See, Akkina et al. (1996) *J Virol* 70:2581; Poznansky et al. (1991) *J Virol* 65:532; Parolin et al. (1994) *Journal of Virology* 68:3888; Richardson et al. (1995) *Journal of General Virology* 76:691; Buchschacher et al. (1992) *Journal of Virology* 66:2731; and Marlink et al. (1994) *Science* 265:1587.

Stem cells are isolated for transduction and differentiation using known methods. For example, in mice, bone marrow cells are isolated by sacrificing the mouse and cutting the leg bones with a pair of scissors. Stem cells are isolated from bone marrow cells by panning the bone marrow cells with antibodies which bind unwanted cells, such as CD4+ and CD8+ (T cells), CD45+ (panB cells), GR-1 (granulocytes), and $Ia^d$ (differentiated antigen presenting cells). For an example of this protocol see, Inaba et al. (1992) *J. Exp. Med.* 176, 1693–1702.

In humans, bone marrow aspirations from iliac crests are performed e.g., under general anesthesia in the operating room. The bone marrow aspiration is approximately 1,000 ml in quantity and is collected from the posterior iliac bones and crests. If the total number of cells collected is $<2\times10^8$, a second aspiration using the sternum and anterior iliac crests in addition to posterior crests is performed. During the operation, two units of irradiated packed red cells are administered to replace the volume of marrow taken by the aspiration. Human hematopoietic progenitor and stem cells are characterized by the presence of a CD34 surface membrane antigen. This antigen is used for purification, e.g., on affinity columns which bind CD34. After the bone marrow is harvested, the mononuclear cells are separated from the other components by means of ficol gradient centrifugation. This is performed by a semi-automated method using a cell separator (e.g., a Baxter Fenwal CS3000+ or Terumo machine). The light density cells, composed mostly of mononuclear cells are collected and the cells are incubated in plastic flasks. The adherent cells (monocytes, macrophages and B-Cells) are discarded. The non-adherent cells are then collected and incubated with a monoclonal anti-CD34 antibody. After two washes, paramagnetic microspheres (Dyna Beads, supplied by Baxter Immunotherapy Group, Santa Ana, Calif.) coated with sheep antimouse IgG (Fc) antibody are added to the cell suspension at a ratio of 2 cells/bead. After a further incubation period, the rosetted cells with magnetic beads are collected with a magnet. Chymopapain (supplied by Baxter Immunotherapy Group, Santa Ana, Calif.) at a final concentration of 200 U/ml is added to release the beads from the CD34+ cells. Alternatively, and also preferably, an affinity column isolation procedure can be used which binds to CD34, or to antibodies bound to CD34.

In another embodiment, hematopoietic stem cells are isolated from fetal cord blood. Yu et al. (1995) *PNAS* 92: 699–703 describe a method of transducing CD34+ cells from human fetal cord blood using retroviral vectors.

Rather than using stem cells, T cells are also used in preferred embodiments in ex vivo procedures. Retroviral vectors which comprise HIV Env protein on the surface of the vector are typically used for transducing CD4+ cells. Env protein can be incorporated into a retroviral vector by pseudotyping the vector by expressing Env protein in the packaging cell used to make the retroviral vector.

Several techniques are known for isolating T cells. In one method, Ficoll-Hypaque density gradient centrifugation is used to separate PBMC from red blood cells and neutrophils according to established procedures. Cells are washed, and enriched by negative or positive selection with appropriate monoclonal antibodies coupled to columns or magnetic beads according to standard techniques. An aliquot of cells is analyzed for desired cell surface phenotype (e.g., CD4 expression, etc.).

Where the cells are isolated from an HIV+ patient, CD4-PE40 (a recombinant protein consisting of the HIV-1-binding CD4 domain linked to the translocation and ADP-ribosylation domains of *Pseudomonas aeruginosa* exotoxin A), or another cytotoxic molecule which targets HIV infected cells, is optionally added to the cell cultures for the remainder of the cell expansion to selectively remove HIV infected cells from the culture. CD4-PE40 inhibits p24 production in HIV-1-infected cell cultures and selectively kills HIV-1-infected cells.

To stimulate proliferation, OKT3 monoclonal antibody (Ortho Diagnostics) is optionally added. The cells are cultured under standard conditions (e.g., at 37° C. in an incubator with 5% $CO_2$).

The expression of surface markers facilitates identification and purification of T cells. Methods of identification and isolation of T cells include FACS, column chromatography, panning with magnetic beads and the like. For a review of immunological and immunoassay procedures in general, see Stites and Terr (eds.) 1991 *Basic and Clinical Immunology* (7th ed.) and Paul supra. For a discussion of how to make antibodies to selected antigens see, e.g. Coligan (1991) Current Protocols in Immunology Wiley/Greene, New York; and Harlow and Lane (1989) *Antibodies: A Laboratory Manual* Cold Spring Harbor Press, N.Y.; Stites et al. (eds.) Basic and Clinical Imnmunology (4th ed.)

Administration of The Targeted Molecules, Gene Therapy Vectors, and Ex Vivo Transduced Cells of the Invention as Therapeutic Agents The targeted molecules of the invention, transduced cells (e.g., CD34+ or CD4+ cells), and gene therapy vectors of the invention are all optionally administered to a patient to alleviate retroviral infection, or to act as a prophylactic against retroviral infection. The patient is typically a human, but veterinary applications where the retrovirus to be inhibited infects a non-human animal, such as a mammal or bird, are also appropriate.

Administration of transduced cells, targeted molecules, or gene therapy vectors is by any of the routes normally used for introducing a molecule into ultimate contact with blood or tissue cells. Suitable methods of administering such packaged nucleic acids in the context of the present invention to a patient are available and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

In the practice of this invention, compositions can be administered, for example, by intravenous infusion, orally, topically, intraperitoneally, intravesically or intrathecally. The preferred method of administration will often be oral, rectal or intravenous, but the vectors can be applied in a suitable vehicle for the local and topical treatment of virally-mediated conditions. The compositions of this invention (e.g., transduced cells, cell transformation vectors, and targeted molecules) can supplement treatment of virally-mediated conditions by any known conventional therapy, including cytotoxic agents, nucleotide analogues and biologic response modifiers.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, filers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. Oral administration is not appropriate for introducing transduced cells of the invention into a patient, but can be used, e.g., for administration of targeted molecules.

The gene therapy vectors and targeted molecules of the invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration of targeted molecules and gene therapy vectors include, for example, suppositories, which consist of the active therapeutic ingredient with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Parenteral administration and intravenous administration are the preferred methods of administration for many compounds, and for the gene therapy vectors of the invention. Formulations can be presented in unit-dose or multi-dose sealed containers, such as ampules and vials.

Injection solutions and suspensions can be prepared from sterile powders, granules, and tablets of the kind previously described. Cells transduced by the nucleic acids of the invention, as described above in the context of ex vivo therapy are preferably administered intravenously or parenterally as described above.

The dose administered to a patient, in the context of the present invention should be sufficient to effect a beneficial therapeutic response in the patient over time, or to inhibit infection by a selected retrovirus. The dose will be determined by the efficacy of the particular vector or targeted molecule employed and the condition of the patient, as well as the body weight or surface area of the patient to be treated. The size of the dose also will be determined by the existence, nature, and extent of any adverse side-effects that accompany administration of a particular vector, composition, or transduced cell type in a particular patient.

In determining the effective amount of vector, transduced cell type or targeted molecule to be administered in the treatment or prophylaxis of virally-mediated diseases such as AIDS, the physician evaluates circulating plasma levels, toxicities of the therapeutic compounds, and progression of the disease. In general, the dose equivalent of a naked nucleic acid from a vector of the invention is from about 1 $\mu$g to 1 mg for a typical 70 kilogram patient, and doses of vectors which include a vector particle (e.g., a retroviral capsid and envelope, or an AAV capsid) are calculated to yield an equivalent amount of nucleic acid which encodes an oligonucleotide decoy of the invention. Doses for the targeted molecules of the invention are typically from about 1 picomole to about 1 milimole of targeted molecule for a typical 70 kilogram patient.

For administration, inhibitors and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

In ex vivo procedures, transduced cells are re-infused into the patient. Prior to infusion, blood samples are obtained and saved for analysis. Between $1\times10^8$ and $1\times10^{12}$ transduced cells are typically infused intravenously over 60–200 minutes. Vital signs and oxygen saturation by pulse oximetry are closely monitored. Blood samples are obtained 5 minutes and 1 hour following infusion and saved for subsequent analysis.

Cell isolation, transduction and reinfusion are repeated every 2 to 3 months for a total of 4 to 6 treatments in a one year period. After the first treatment, infusions can be performed on a outpatient basis at the discretion of the clinician. If the reinfusion is given as an outpatient, the participant is monitored for at least 4, and preferably 8 hours following the therapy.

Transduced cells are prepared for reinfusion according to established methods. See, Abrahamsen et al. (1991) *J. Clin. Apheresis* 6:48–53; Carter et al. (1988) *J. Arpheresis* 4:113–117; Aebersold et al. (1988), *J. Immunol. Methods* 112: 1–7; Muul et al. (1987) *J. Immunol. Methods* 101:171–181 and Carter et al. (1987) *Transfusion* 27:362–365. After a period of about 2–4 weeks in culture, the cells should number between $1\times10^8$ and $1\times10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

If a patient undergoing infusion of composition develops fevers, chills, or muscle aches, he/she should receive the appropriate dose of aspirin, ibuprofen or acetaminophen. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Infusion of the composition is slowed or discontinued depending upon the severity of the reaction.

EXAMPLES

The following examples are provided by way of illustration only and not by way of limitation. Those of skill will readily recognize a variety of noncritical parameters which can be changed or modified to yield essentially similar results.

EXAMPLE 1
Surface Plasmon Resonance Assessment of Oligonucleotide Binding

NC has traditionally been described as a single-stranded nucleic acid-binding protein. To determine whether this conclusion is accurate under SPR conditions, we initially measured binding of recombinant HIV-1 NC to a single-stranded 28-base oligodeoxynucleotide. The sequence of this oligonucleotide contains 20 bases from the 3' end of HIV-1 proviral DNA (i.e., the 3' end of U5). Surface plasmon resonance (SPR) analysis was performed with biotinylated DNA immobilized at its 3' end.

As shown in FIG. 1A, NC bound to this oligonucleotide under the conditions of the experiment. In the initial phase of the experiment (when NC solution is being passed across the oligonucleotide containing surface), several NC molecules bound to the oligonucleotide (the horizontal line in FIG. 1A (as well as the other figures, supra) represents the response if a single NC molecule bound to each oligonucleotide molecule.) Some of the bound NC was rapidly released during the second ("washout") phase of the experiment (when the NC solution is replaced by SPR buffer). However, examination of the curves shows that a significant portion of the NC is released quite slowly; further, this amount is practically the same in the curves obtained at NC concentrations between 25 and 200 nM. This observation suggests that there are a limited number of high-affinity binding sites on the 28-base oligonucleotide; these sites are evidently almost fully occupied at NC concentrations as low as 25 nM. Additional binding occurs at higher NC concentrations, but this attachment is evidently at considerably lower affinity, since this portion of the NC is easily removed during the washout. Extrapolation of the shallow portion of the washout curves (representing removal of the tightly bound NC molecules) to the beginning of the washout step suggests that the high-affinity binding involves two NC molecules per oligonucleotide.

To test the preference of NC for single—rather than double-stranded nucleic acids under our experimental conditions, we also measured its ability to bind a double-stranded form of the 28-base oligonucleotide. An oligonucleotide complementary to the original 28-base sequence was added to the SPR chip used in the experiment shown in FIG. 1A. Hybridization to the DNA already on the chip was confirmed by an increase in mass on the chip detected by SPR. As shown in FIG. 1B, NC exhibited only negligible binding to this double-stranded DNA; it thus shows a strong preference for single-stranded DNA. The data also indicate that the protein does not significantly dissociate the two strands of this 28-base-pair DNA molecule.

A. Demonstration of Sequence-Specific High-Affinity Binding of NC to Single-Stranded Oligodeoxynucleotides: Partial Analysis of Sequence Preference.

NC has frequently been described as binding to single-stranded nucleic acids at a ratio of one NC molecule per ~7 nucleotide residues, with little or no sequence specificity. Thus, it was surprising that the results presented above indicated the presence of one or two high-affinity binding sites in the 28-base oligonucleotide, rather than four. One possible explanation of these findings is that the occluded site size under our experimental conditions is ≧14, rather than ~7 bases; alternatively, NC might bind to the ~7-base sites with significantly different affinities, and the oligonucleotide under study might contain only one or two such sites with affinities high enough to be detected using the present methods. To test this possibility, we subdivided the 28-base sequence into three smaller sequences, and tested binding to each of them. Three oligonucleotides, containing sequences from the 5', middle, and 3' regions of the 28-base sequence (designated sites I, II, and III, respectively), were analyzed, with the SPR results shown in FIG. 2A–C. Site I, i.e., GACTTGTGG, showed the most stable binding (FIG. 2A); site II, i.e., AAAATCTCTA (SEQ ID NO:15), showed negligible binding (FIG. 2B); and site III, i.e., GCAGTGCAT, showed significant binding, but at a lower level and a more rapid loss during the washout than was observed with site I (FIG. 2C). The results show clearly that sequences far shorter than 14 bases are sufficient for high-affinity binding, and that there are profound differences in the affinity with which NC binds to different sequences.

Figure 2:
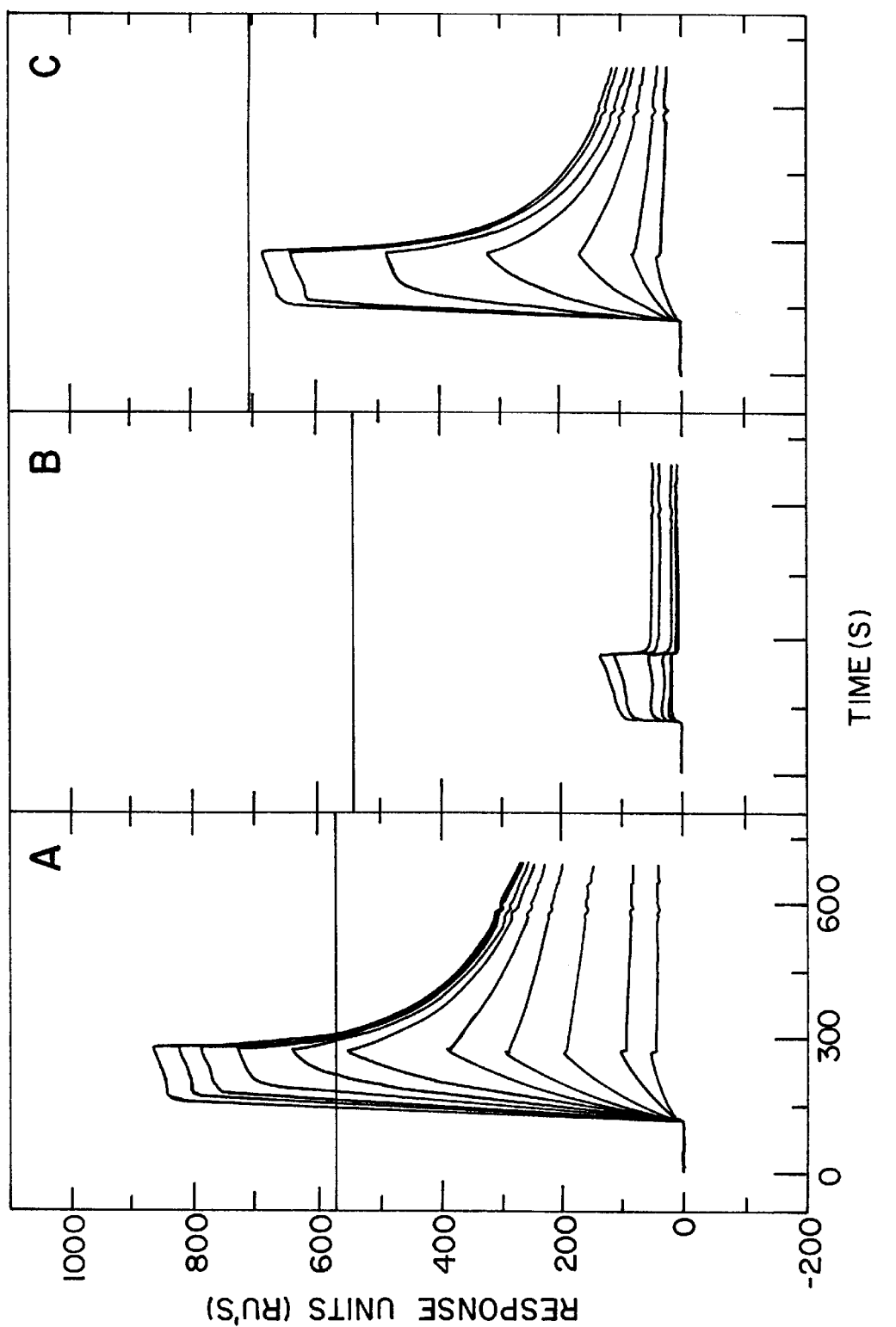
FIG. 2, Panels A–C show graphs of NC binding to 28 mer.
Figure 3:
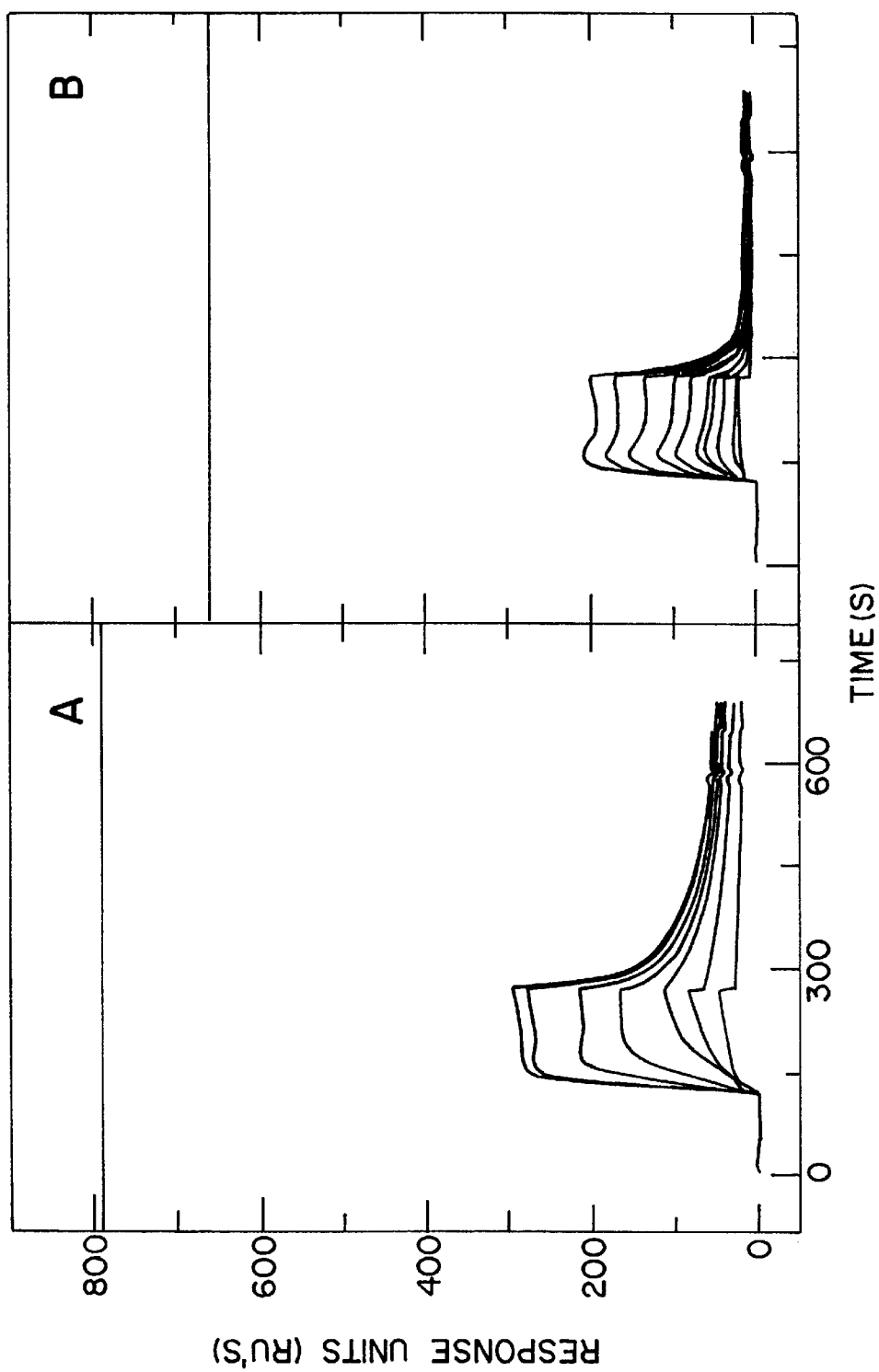
FIG. 3, Panels A and B show graphs of NC binding to $dG_9$ or $dT_{10}$ (SEQ ID NO:12) under BIAcore conditions.

The results shown in FIG. 2 demonstrate a striking preference for the oligonucleotides containing G residues; indeed, the higher affinity for the 5' site than for the 3' site correlates with the higher G (and possibly T) content of this sequence. To determine whether the binding preference for site I (FIG. 2A) could be attributed to the G (and T) content of this sequence we measured binding to the four homopolymeric oligodeoxynucleotides by SPR (FIG. 3). As can be seen, NC exhibited a clear preference for $d(G)_9$ over the other homopolymers under these conditions, and also showed detectable binding to $d(T)_{10}$ (SEQ ID NO:12). However, both the extent of the binding to $d(G)_9$ (relative to the horizontal line in the Figure, which would be the SPR signal obtained upon binding of one NC molecule to each oligonucleotide molecule on the chip) and the retention of NC during the washout were far lower than seen with site 1 sequences. These results demonstrate that NC possesses a true sequence-specific component in its interaction with single-stranded DNA.

Figure 4:
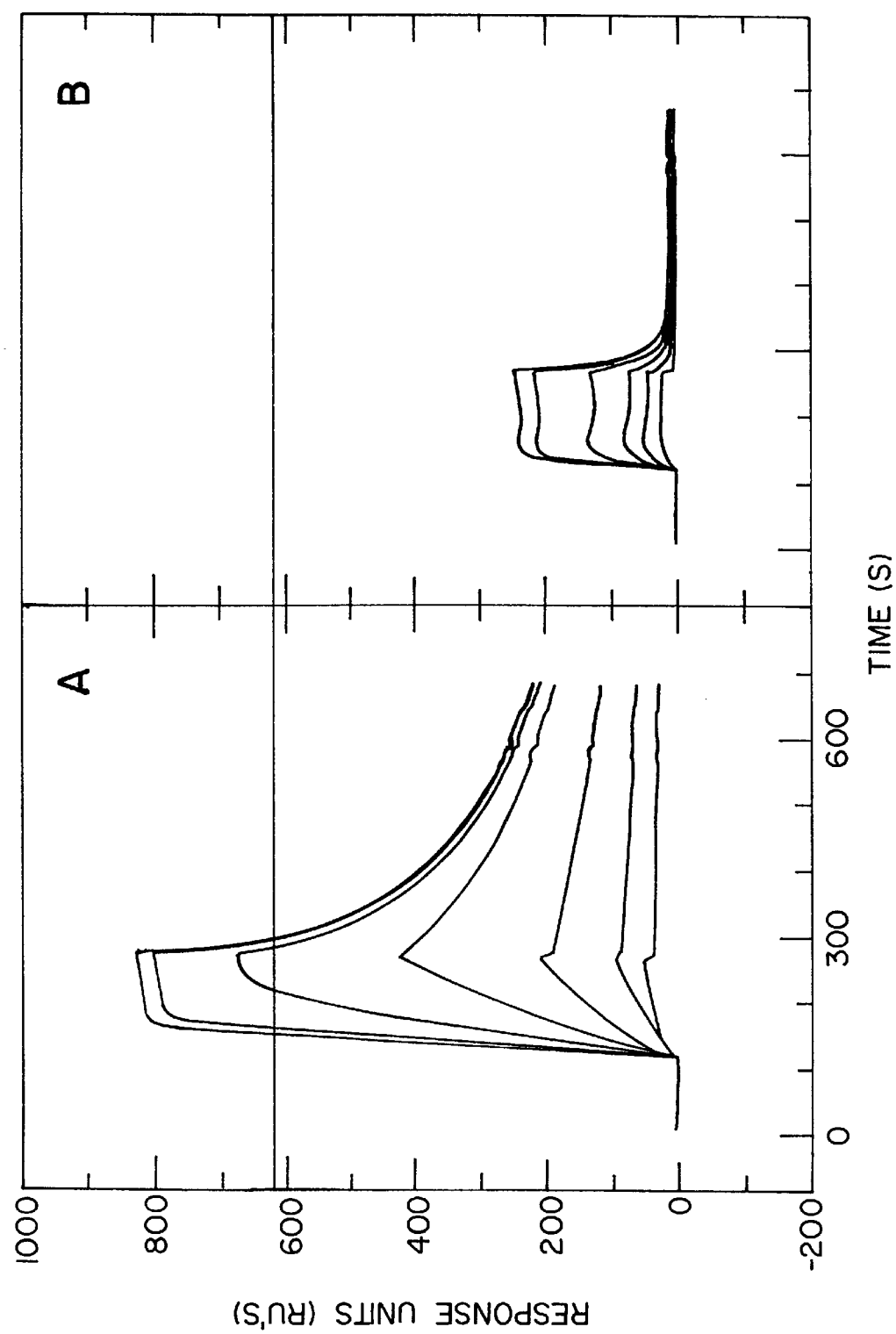
FIG. 4, Panels A and B show graphs of NC binding to AAAATGTGAA (SEQ ID NO:13)but not to GACTAAAAGA (SEQ ID NO:14).

Comparison with binding to other oligonucleotides raised the possibility that the presence of the sequence TGTG (SEQ ID NO:3) within the 5' site was responsible for high-affinity binding to this site. To test this possibility, SPR analysis of the binding to two additional oligonucleotides was performed: one in which the TGTG (SEQ ID NO:3)within the site was replaced by AAAA, and one in which the six bases other than TGTG (SEQ ID NO:3) were replaced by A's. The results of these tests are shown in FIG. 4, and show that TGTG (SEQ ID NO:3) is necessary and sufficient for high-affinity binding to a ten-base oligonucleotide, even if the other bases are all A's, to which NC binds very poorly (FIG. 4).

Figure 5:
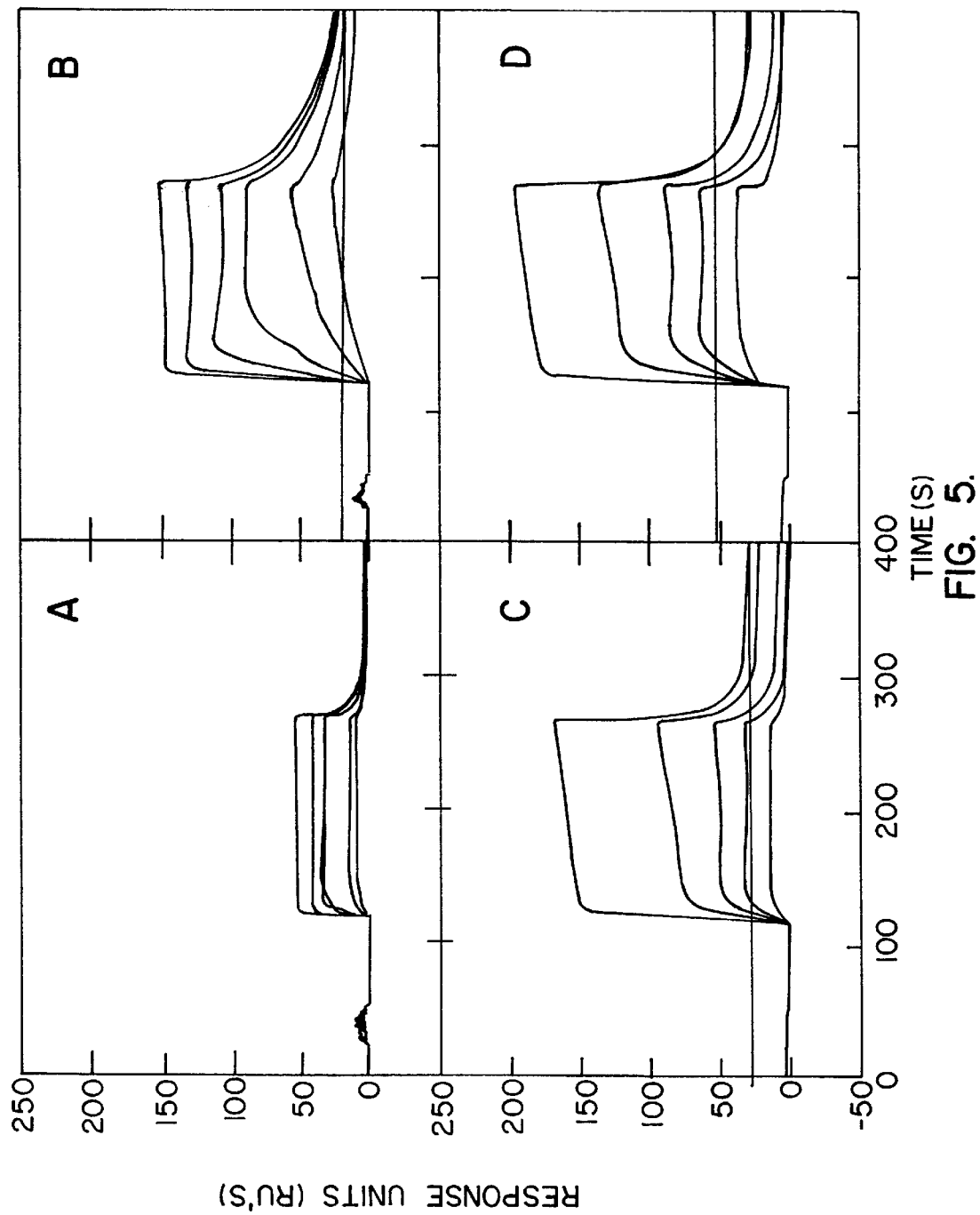
FIG. 5, Panels A–D show graphs of NC binding to TGTGT (SEQ ID NO:4) or GTGTG (SEQ ID NO:5) as sufficient for stable binding.

To determine the minimal length of oligonucleotide composed of alternating T's and G's which was capable of retaining a molecule of NC at high affinity, we tested different lengths of DNA containing only this sequence. As shown in FIG. 5, we found that either of two pentanucleotides, i.e., TGTGT (SEQ ID NO:4) or GTGTG (SEQ ID NO:5), constitute high-affinity binding sites for NC, each binding a single NC molecule with roughly equivalent affinities. In addition, we found that only one NC molecule binds to the octamer $(TG)_4$ (SEQ ID NO:6), but two bind to $(TG)_5$ (SEQ ID NO:7) and four bind to $(TG)_{10}$ (SEQ ID NO:8) (Table 1). These results demonstrate that with this sequence, 5 bases are sufficient for high-affinity binding, and that each NC molecule "occupies" a stretch of only 5 bases under our experimental conditions.

B. "Crosslinking" of Short Oligonucleotides by NC.

Figure 6:
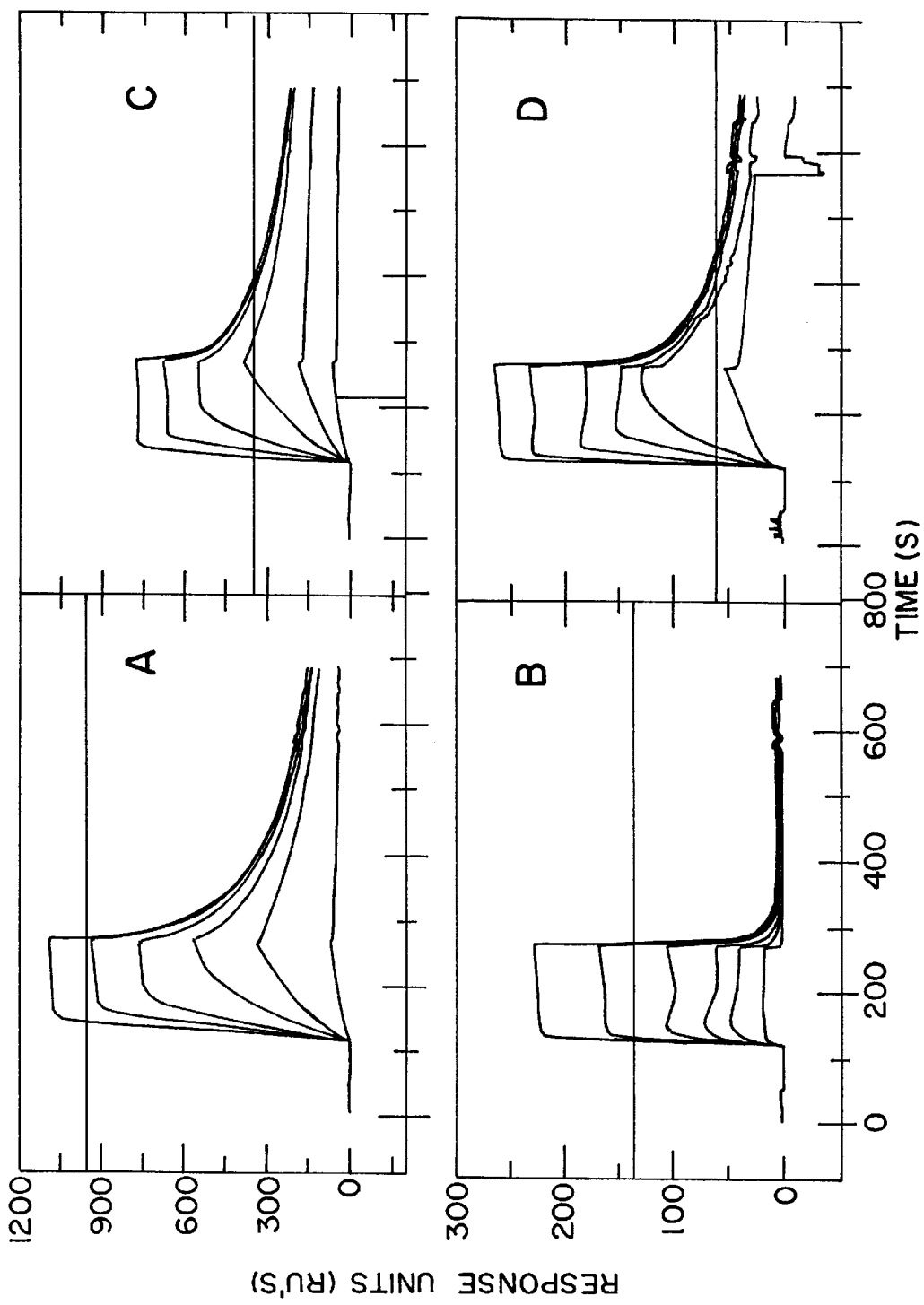
FIG. 6, Panels A–D show by graphs that NC binding to TGTG is surface density dependent.

In the course of experiments to define a minimal high-affinity binding site for NC, we found that initial experiments with the tetranucleotide TGTG (SEQ ID NO:3) failed to give reproducible results. Further investigation suggested that the apparent affinity of NC for TGTG (SEQ ID NO:3) was a function of the concentration of the oligonucleotide during SPR analysis. This possibility was analyzed systematically in the following experiment. Four SPR chips were made containing TGTG (SEQ ID NO:3) at different densities. For each chip, the amount of streptavidin (which holds the biotinylated oligonucleotide on the chip) was measured by SPR analysis before the addition of TGTG (SEQ ID NO:3). The amount of TGTG (SEQ ID NO:3) added to each chip was then quantitated by SPR. Thus, for each chip the ratio of TGTG (SEQ ID NO:3) to streptavidin was empirically determined. Since a streptavidin molecule has four binding sites for biotinylated ligands, the number of streptavidin molecules occupied by 0, 1, 2, 3, or 4 oligonucleotides could be calculated from this ratio, using binomial expansion. Finally, the ability of each chip to bind NC with high affinity was determined by SPR. The results of this experiment are shown in FIG. 6; the inset in each panel shows the predicted frequency distribution of oligonucleotides on streptavidin molecules. Inspection of the four curves shows clearly that high-affinity binding is achieved at the highest density (FIG. 6D) and not at the lowest density (FIG. (6A); quantitative analysis indicates that the level of high-affinity binding seen with each chip can be completely accounted for by streptavidin molecules containing two or more oligonucleotides. In contrast, binding to longer oligonucleotides, including TGTGTGTG (SEQ ID NO:6) and site I, i.e., GACTTGTGG, was essentially independent of the densities of these DNAs during SPR analysis. We conclude that if two short oligonucleotides containing alternating T's and G's are close enough to each other, they can jointly participate in high-affinity binding to NC.

FIG. 6A also shows that NC shows a substantial degree of initial binding to TGTG (SEQ ID NO:3), even when the latter is present at low density. Thus, the data demonstrate a difference between level of binding and affinity of binding.

C. High-affinity Binding Depends on Zinc Fingers in NC.

HIV-1 NC contains two zinc fingers. Mutational analysis shows that these structures are of crucial importance in vivo, participating both in packaging of genomic RNA during virus assembly and in some additional step(s) during the infectious process. However, studies in vitro have given little evidence of a significant role for the fingers in interactions of NC with nucleic acids in vitro. To test their importance for the high-affinity, sequence-specific binding described in the present study, we analyzed binding of three "finger swap" mutants of NC to the 5' site. These mutant proteins contain two zinc fingers, but in "1.1", the C-terminal finger has been replaced with a second copy of the N-terminal finger. "2.2" has an analogous duplication of the C-terminal finger, while in "2.1", both fingers are present, but their positions in the protein have been reversed.

Figure 7:
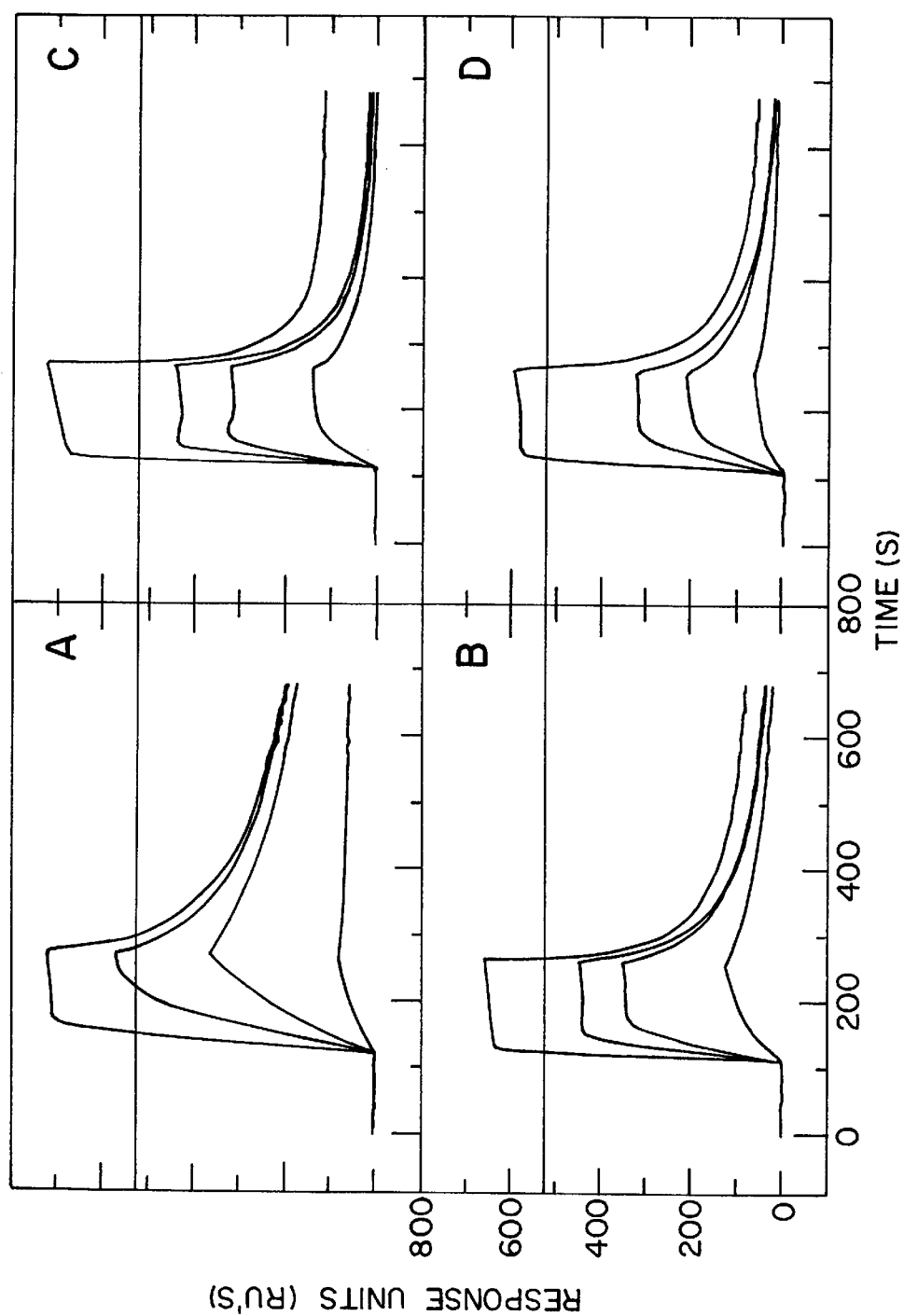
FIG. 7, Panels A–D show graphs demonstrating that Zinc Finger swap mutants do not stably bind to GACTTGTGG.

Results of this experiment are shown in FIG. 7. The data show that the mutant proteins all exhibit some binding to the 5' site, but in every case the mutants (FIG. 7A–C) washed out considerably faster than the wild-type protein (FIG. 7D).

As an additional test of the role of the zinc fingers in the high-affinity binding of NC to DNA, we performed SPR analysis in the presence of EDTA. No significant binding to the 28-base oligonucleotide was observed when 1 $\mu$M NC was tested in the presence of 3.3 mM EDTA (data not shown). This result supports the hypothesis that the specific binding we observed is dependent upon intact zinc fingers within NC.

D. Analysis of High-Affinity Binding by Fluorescence.

As a completely independent way of studying the interaction between NC protein and oligonucleotides, we measured the change in tryptophan fluorescence upon stepwise addition of oligonucleotide to NC solutions. The initial titration was performed in 0.01 M sodium phosphate, but after saturation of the protein with oligonucleotide, NaCl was added and the dissociation of the protein-nucleic acid complex was monitored by fluorescence. This approach allowed us to determine the apparent affinity of the protein for a given oligonucleotide at a wide range of salt concentrations. As with the SPR results, the oligonucleotide for which NC had the highest affinity was $d(TG)_4$ (SEQ ID NO:6), and the protein also bound with relatively high affinity to site I. The affinity for $dG_9$ was higher than that for the other hompolymeric oligodeoxynucleotides. Binding of the 2.2 finger swap mutant protein to site I gave a lower apparent affinity than that of wild-type protein.

E. Sequence-Specific High-affinity Binding Has a Major Hydrophobic Component.

Since fluorescence analysis included a determination of the sensitivity of NC-oligonucleotide binding to increasing ionic strength, it was possible to estimate the contributions of ionic and hydrophobic interactions to the binding. All of the oligonucleotides, including three octanucleotides with alternating sequences and homopolymeric octanucleotides containing each of the bases represented in the alternating sequences, showed similar ionic components, expressed as $\delta(\log K)/\delta(\log [Na^+])$. In contrast, the hydrophobic components, representing the apparent affinity constants at 1M NaCl(K°) for binding to the octanucleotides, varied over nearly three orders of magnitude, i.e., between $5 \times 10^1$ for $(dT)_9$ and $2.3 \times 10^4$ for $d(TG)_4$ (SEQ ID NO:6).

We also compared the K° values for the alternating-sequence oligonucleotides with the weighted averages of the corresponding homopolymers, e.g., $d(GA)_4$ vs. $dG_8/dA_9$. The hydrophobic component for binding to $d(GA)_4$, coincided with the value that would be predicted from the average of $dG_8$ and $dA_9$. However, the K° for $d(TG)_4$ (SEQ ID NO:6) was 145 times higher than the expected value; thus, the additional binding energy for $d(TG)_4$ (SEQ ID NO:6) is largely hydrophobic.

To gain further insight into the specific binding of NC to $d(TG)_4$ (SEQ ID NO:6), we also measured the binding of NC to a related oligonucleotide, i.e., $d(IT)_4$. As shown in Table 2, the K° for $d(IT)_4$ was 10 times higher than the average of that for $d(I)_8$ and for $d(T)_8$. Thus, a large fraction of the hydrophobic interaction of NC with $d(TG)_4$ (SEQ ID NO:6) evidently involves the exocyclic amino group on guanine.

F. Example High-Affinity Binding of NC to RNA.

Figure 8:
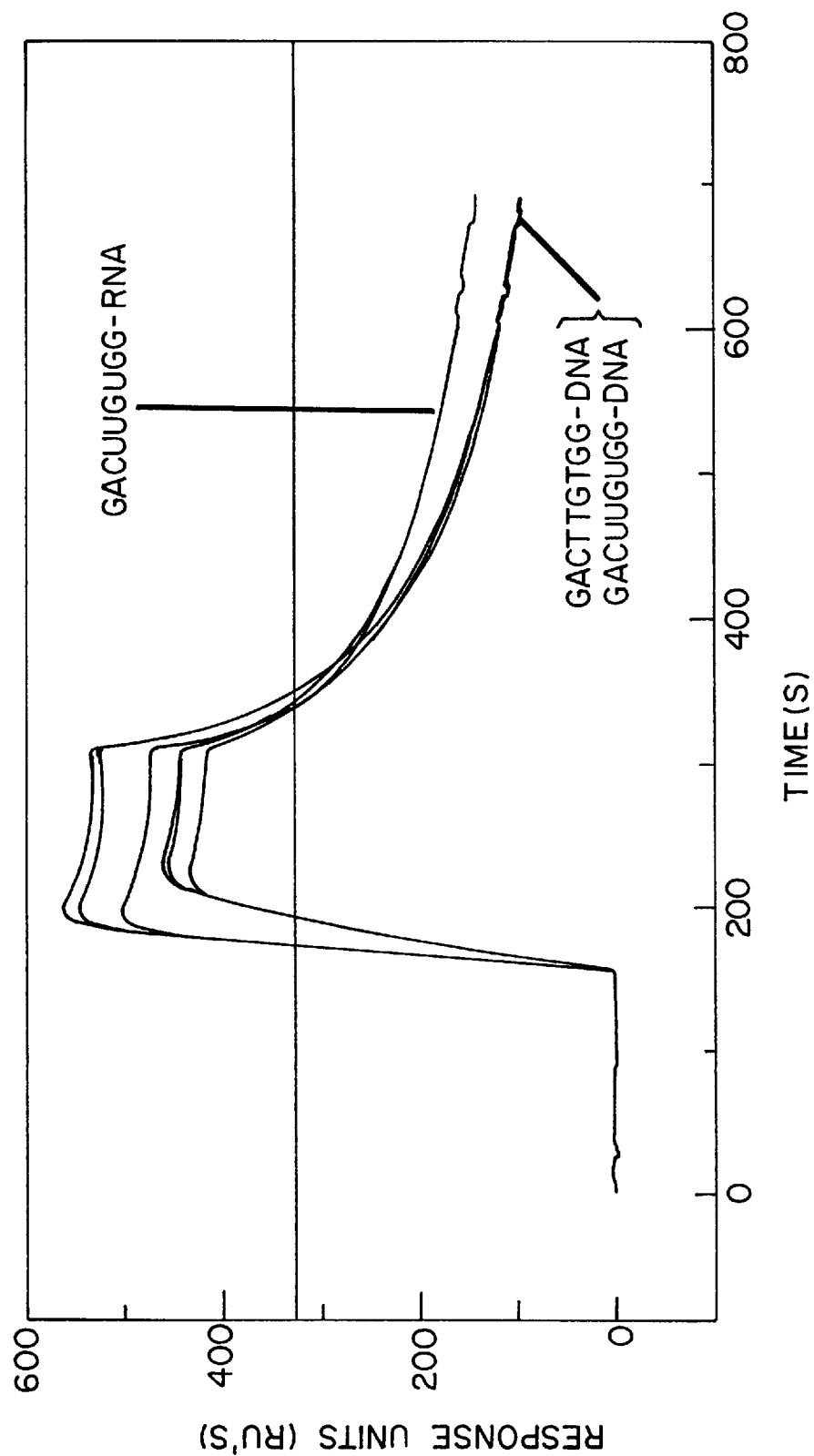
FIG. 8 shows a graph demonstrating that NC binds RNA (GACUUGUGG=SEQ ID NO:11).

It was of interest to determine whether the sequences to which NC binds with high affinity in DNA would also constitute high-affinity sites in RNA. Therefore, we tested binding of NC to the RNA analog of site I, i.e., GACU-UGUGG (SEQ ID NO:11). As shown in FIG. 8, the binding to the RNA oligonucleotide is actually at a higher level and washes out more slowly than the binding to the DNA. Thus, it seems the binding characteristics of NC which we have described using short DNA molecules apply to RNA binding as well.

G. Discussion

In this example we have analyzed the binding of recombinant HIV-1 NC protein to very short oligonucleotides. Two fundamentally different techniques, i.e., SPR analysis and fluorescence were used in parallel in these experiments. An alternating sequence of T's and G's gave the most stable binding detected. The affinity for this sequence is at least 100 times that of some other sequences and represents a true sequence preference, rather than a preference for the bases T and/or G, since the affinity is far higher than that for T or G-containing homopolymers.

This high-affinity, sequence-specific binding involves the zinc fingers in NC, since it is not observed with proteins with rearranged zinc fingers (FIG. 7) or when $Zn^{+2}$ is removed from the wild-type protein with EDTA. The failure of all three "finger switch" proteins to bind to site I with the same high affinity as that of wild-type NC demonstrates that both fingers must be present, each in its proper position in the protein, for the high-affinity binding. The discovery of an in vitro activity of NC which is dependent on the zinc fingers is quite significant, as these structures are of crucial importance in vivo, but are dispensable for most of the NC-nucleic acid interactions which have been analyzed previously in vitro.

The hydrophobic contribution to the high-affinity binding seen with d(TG)$_4$ (SEQ ID NO:6) is far higher than with binding to other oligodeoxynucleotides, including d(GA)$_4$ as well as a series of homopolymeric oligonucleotides. Indeed, this contribution is significantly higher with d(TG)$_4$ (SEQ ID NO:6) than with d(IT)$_4$. Since there is presumably no "polarity" in the binding of NC to these alternating sequences, this observation suggests that the exocyclic amino group by which G differs from I is involved in the high-affinity binding to d(TG)$_4$ (SEQ ID NO:6). The difference in binding energy inferred from the difference in affinity for the two octanucleotides is ~1 kcal/mole; this would be consistent with participation of the amino group in a hydrogen bond with a residue in NC.

As part of our characterization of the binding of NC to deoxynucleotides containing alternating T's and G's, we identified a minimum length required for high affinity binding. We found that pentanucleotides, i.e., either TGTGT (SEQ ID NO:4) or GTGTG (SEQ ID NO:5), were capable of high-affinity interaction with NC (FIG. 5). This value of five as the minimum number of bases required for high-affinity interaction is somewhat lower than 7–8, the value found in a number of studies for the "occluded site size", or average number of bases per NC molecule when a nucleic acid is saturated with NC. While this is the first time the number of bases occupied by NC has been determined with this degree of precision, it seems likely that the discrepancy between our results and those in the literature is real: NC may be more compact or NC molecules may be crowded together more tightly when engaged in high-affinity binding to a preferred sequence.

We also found that NC could bind stably to the tetranucleotide d(TG)$_2$ (SEQ ID NO:3), but only if the TGTG (SEQ ID NO:3) molecules were in close proximity to each other (FIG. 6). This observation shows that a single NC molecule can simultaneously bind or "cross-link" two such oligonucleotides. This conclusion was confirmed by the fact that the stoichiometry of the complex formed at equilibrium between NC and TGTG (SEQ ID NO:3) is 1:2, as measured by fluorescence. The simultaneous binding of a single NC molecule to two tetranucleotides could mean that NC has a single nucleic acid binding site, requiring at least 5 bases for stable interaction. Alternatively it could have two binding sites requiring 4 bases for stable interactions.

Finally, we tested an RNA corresponding to a high-affinity DNA sequence. The affinity of NC for this RNA was significantly greater than for the DNA (FIG. 8). This result shows that the results obtained here with DNA are applicable to interaction with RNA as well.

We have subjected the SPR data obtained with d(TG)$_4$ (SEQ ID NO:6) to a detailed quantitative analysis. This analysis shows that NC can bind to this oligonucleotide in two distinct ways. These two binding systems are independent of each other, in essence competing with each other for the NC molecules. One of these systems is primarily responsible for the slow, washout from d(TG)$_4$ (SEQ ID NO:6) and exhibits a $K_a$ of $2 \times 10^9$ $M^{-1}$. The other has a $K_a$ of only $1 \times 10^7$, representing the fraction of NC molecules which are released more rapidly during the washout phase.

Another important aspect of the experiments described here is that the analyses were performed in 0.15M NaCl. The sequence-independent electrostatic interaction between the positively charged NC protein and nucleic acids is obviously much lower at this moderate ionic strength than in more dilute buffers, so that the differences in affinity for different oligonucleotides are more apparent. Indeed, analysis of the salt dependence of binding of NC to a series of oligonucleotides showed that the electrostatic components were all very similar, but the hydrophobic components varied widely. The additional affinity of NC for a preferred sequence was shown by this analysis to be largely hydrophobic.

It is now clear that NC has at least one important function as a domain of the Gag polyprotein, viz. in RNA packaging during virus assembly. Clearly, this function involves a highly specific interaction with a nucleic acid molecule, i.e., genomic RNA. Thus, one possible explanation for the sequence specificity of NC is that it is simply a reflection, or "remnant", of the specificity exhibited by the NC domain of Gag. (However, the specificity detected here for a simple, 5-base alternating sequence seems insufficient to account for the exquisite selectivity of RNA encapsidation during virus assembly.)

Alternatively, the sequence preferences of NC may be important for the functions that the protein performs after it is cleaved from the Gag polyprotein. NC is complexed with the genomic RNA in the ribonucleoprotein core of the mature retrovirus particle, and in this "structural" role it may protect the RNA from nucleases or help to condense it into a small volume in the interior of the particle. It seems likely that, at the high RNA and protein concentrations in the viral core, NC is bound to the entire genomic RNA, regardless of sequence.

However, NC also has activity as a nucleic acid chaperone. That is, it lowers the energy barrier for breakage and reformation of base pairs in nucleic acids, enabling it to catalyze the rearrangement of a nucleic acid molecule into the structure with the maximum number of base pairs. This activity is known to be at work during virus maturation, when the dimeric genomic RNA undergoes a stabilization event. In addition, in vitro studies strongly suggest that the chaperon activity is important during reverse transcription of the genomic RNA in the newly infected cell. It seems possible that the binding of NC to preferred sequences is related to its functions as a nucleic acid chaperon. For example, the sequence preferences might serve to localize the protein at sites where its chaperon activity is required; alternatively, the chaperon activity might result in the exposure of high-affinity sites, for example during reverse transcription.

It is interesting to note that alternating (UG) sequences are found at several sites in HIV-1 genomic RNA; one of these is at the extreme 3' end of U5 (most of the sequence of the 28-base oligodeoxynucleotide used in our initial experiments is from this portion of the genome). Another is in a more 5' position in U5. The function of this highly conserved sequence is not known, but it is important for the virus, since subtle changes lead to a profound diminution in replicative capacity. Similar sequences are also found in "stem-loop 3", a region in the leader which appears to be important for encapsidation of the genome.

In summnary, the binding of NC to nucleic acids exhibits profound sequence preferences. This sequence-specific interaction is remarkably complex at the biochemical level, and. its biological significance is unknown at present. The high-affinity binding described here can be exploited in the development of new approaches to both detection and growth-inhibition of HIV-1.

All publications and patent applications cited in this specification are herein incorporated by reference as if each individual publication or patent application were specifically and individually indicated to be incorporated by reference in its entirety for all purposes. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A targeted molecule comprising an oligonucleotide which binds to a retroviral nucleocapsid protein with high affinity, and a fusion partner, wherein the targeted molecule binds to the retroviral nucleocapsid protein with high affinity.

2. The targeted molecule of claim 1, wherein the fusion partner chemically reacts with the retroviral nucleocapsid protein, thereby reducing the ability of the nucleocapsid protein to package retroviral RNA.

3. The targeted molecule of claim 1, wherein the fusion partner is cytotoxic.

4. The targeted molecule of claim 1, wherein the fusion partner is a protein.

5. The targeted molecule of claim 1, wherein the oligonucleotide is a GT rich DNA oligonucleotide, or a GU rich RNA oligonucleotide.

6. The targeted molecule of claim 1, wherein the oligonucleotide is selected from the group consisting of a tetranucleotide, a pentanucleotide, a hexanucleotide, a heptanucleotide and an octanucleotide.

7. The targeted molecule of claim 1, wherein the oligonucleotide comprises a sequence selected from the group of sequences consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

8. The targeting molecule of claim 1, wherein the targeted molecule binds to HIV-1 nucleocapsid (NC) with high affinity.

9. The targeting molecule of claim 1, wherein the fusion partner is a label.

10. The targeting molecule of claim 1, wherein the targeting molecule further comprises a label.

11. The targeted molecule of claim 1, wherein the fusion partner is selected from the group consisting of:

disulfides having the formula

R—S—S—R;

maleimides having the formula

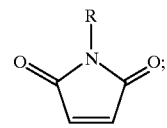

α-halogenated ketones having the formula

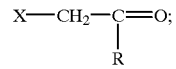

nitric oxide and derivatives containing the NO group;
hydrazides having the formula R—NH—NH—R;
nitroso compounds having the formula R—NO;
cupric ions and complexes containing $Cu^{+2}$;
ferric ions and complexes containing $Fe^{+3}$; and
alkylating agents;
wherein R can be any atom or molecule, and X is a halogen selected from the group consisting of I, F, Br and Cl.

12. A recombinant nucleic acid which encodes an oligonucleotide which binds to a retroviral nucleocapsid protein with high affinity, wherein the nucleic acid comprises a promoter which directs expression of the oligonucleotide in a mammalian cell.

13. The nucleic acid of claim 12, wherein the nucleic acid is packaged in a viral vector.

14. The nucleic acid of claim 12, wherein the nucleic acid is packaged in a retroviral vector.

15. A cell comprising the nucleic acid of claim 12.

16. The cell of claim 15, wherein the cell is a human cell.

17. The cell of claim 15, wherein the cell is a human stem cell.

18. The cell of claim 15, wherein the cell is a human CD4+ cell.

19. A composition comprising a molecular decoy, the molecular decoy comprising an oligonucleotide which binds to a retroviral nucleocapsid protein with high affinity.

20. The composition of claim 19, wherein the molecular decoy is an oligonucleotide with a sequence selected from the group of sequences consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

21. The composition of claim 19, further comprising a protein selected from the group consisting of a nucleocapsid protein, and a Gag protein, wherein the protein is bound to the oligonucleotide.

22. The composition of claim 19, further comprising a pharmaceutical excipient.

23. An assay for detecting target molecules which inhibit binding of an oligonucleotide to a retroviral nucleocapsid protein comprising:

providing a retroviral nucleocapsid protein;

providing an oligonucleotide which binds to the retroviral nucleocapsid protein with high affinity;

providing a target molecule;

mixing the retroviral nucleocapsid protein, oligonucleotide and target molecule; and, measuring the inhibitory effect of the target molecule on oligonucleotide binding to the retroviral nucleocapsid protein.

24. The assay of claim 23, wherein the oligonuclcotide is labeled.

25. The assay of claim 23, wherein the target molecule is selected from the group consisting of oligonucleotides and peptides.

26. The assay of claim 23, wherein the oligonucleotide, target molecule and retroviral protein are mixed in an aqueous solution.

27. The assay of claim 23, wherein the inhibitory effect of the target molecule is measured by plasmon resonance.

28. The assay of claim 23, wherein the assay further comprises parallel analysis of a second target molecule by performing the steps of providing a retroviral nucleocapsid protein;

providing an oligonucleotide which binds to the retroviral nucleocapsid protein with high affinity;

providing a second target molecule;

independently mixing the second target molecule with the retroviral nucleocapsid protein and oligonucleotide; and, measuring the inhibitory effect of the target molecule on oligonucleotide binding to the retroviral nucleocapsid protein.

29. The assay of claim 28, wherein the second target molecule, retroviral nucleocapsid protein and oligonucleotide are mixed in a well on a microtiter tray.

30. A method of detecting a nucleocapsid (NC) protein comprising binding an NC-specific oligonucleotide to the NC protein, thereby forming an NC-oligonuclcotide complex, and detecting the complex, thereby detecting the NC protein.

31. The method of claim 30, wherein the oligonucleotide comprises a detectable label and detection of the NC-oligonucleotide complex is performed by detecting the detectable label.

32. The method of claim 30, wherein the NC protein is a component of an intact retrovirus.

33. The method of claim 30, wherein the NC protein is a Gag precursor protein.

34. The method of claim 30, wherein the NC protein is derived from HIV-1.

35. A method of purifying an NC protein comprising binding an NC-specific oligonucleotide to the NC protein, thereby forming an NC-oligonucleotide complex, and purifying the complex, thereby purifying the NC protein.

36. The method of claim 35, wherein the NC protein is a component of an intact retrovirus.

37. The method of claim 35, wherein the oligonucleotide is linked to a magnetic bead.

* * * * *